US007482138B2

(12) United States Patent
Minden

(10) Patent No.: US 7,482,138 B2
(45) Date of Patent: Jan. 27, 2009

(54) PAK5-RELATED COMPOSITIONS AND METHODS

(75) Inventor: Audrey Minden, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 314 days.

(21) Appl. No.: 10/331,095

(22) Filed: Dec. 27, 2002

(65) Prior Publication Data
US 2003/0124107 A1 Jul. 3, 2003

Related U.S. Application Data

(60) Provisional application No. 60/343,972, filed on Dec. 28, 2001.

(51) Int. Cl.
*C12P 21/06* (2006.01)
(52) U.S. Cl. .................... 435/69.1; 435/6; 435/69.1; 435/320.1; 435/252
(58) Field of Classification Search .................... None
See application file for complete search history.

(56) References Cited

U.S. PATENT DOCUMENTS

| 5,518,911 | A | 5/1996 | Abo et al. .................. 435/194 |
| 5,605,825 | A | 2/1997 | Abo et al. .................. 435/194 |
| 5,698,428 | A | 12/1997 | Abo et al. .................. 435/194 |
| 5,698,445 | A | 12/1997 | Abo et al. .................. 435/325 |
| 6,013,464 | A | 1/2000 | Abo et al. .................. 435/15 |
| 6,013,500 | A | 1/2000 | Minden .................... 435/194 |
| 6,048,706 | A | 4/2000 | Abo et al. .................. 435/15 |
| 6,680,170 | B2 | 1/2004 | Plowman et al. |
| 2003/0050230 | A1 | 3/2003 | Plowman et al. .............. 514/12 |

FOREIGN PATENT DOCUMENTS

| EP | 1085093 A2 | 9/2000 |
| WO | 0073469 A2 | 5/2000 |
| WO | 01/36602 A2 * | 5/2001 |
| WO | 0136602 A2 | 5/2001 |

OTHER PUBLICATIONS

Jaffer et al. Int. J. Biochem. Cell B., vol. 34, pp. 713-717, 2002.*
Pandey et al. Oncogene, vol. 21, pp. 3939-3948, 2002.*
Witkowski et al. Biochemistry, vol. 38, pp. 11643-11650, 1999.*
Dang et al., Clin. Cancer Res., vol. 4, pp. 471-474, 1999.*
Fox, J., Nat. Biotechnol., vol. 21, p. 217, 2003.*
Jan. 10, 2007 Supplementary European Search Report issued in connection with related European Patent Application No. 02794435.4.
Bashour, A.M. et al. (1997) "IQGAP1, a Rac- and Cdc42-binding protein directly bonds and cross-links microfilaments," J. Cell. Biol. 137, 1555-1566.
Benner, G.E. et al. (1995) "Activation of an S6/H4 kinase (PAK 65) from human placenta by intramolecular and intermolecular autophosphorylation," J. Biol. Chem. 270, 21121-21128.
Brown, J. et al. (1996) Human Ste20 homologue hPAK1 links GTPase to JNK MAP kinase pathway. Curr. Biol. 6, 598-605.
Burbelo, P.D. et al. (1995) "A conserved binding motif defines numerous candidate target proteins for both Cdc42 and Rac GTPases," J. Biol. Chem.. 270, 29071-29074.
Cvrckova, F. et al. (1995) "Ste20-like protein kinases are required for normal localization of cell growth and for cytokinesis in budding yeast," Genes Dev. 9, 1817-1830.
Dascher, C. and Balch, W.E. (1994) "Dominant inhibitory mutants of ARF1 block endoplasmic reticulum to Golgi transport and trigger disassembly of the Golgi apparatus," J. Biol. Chem. 269, 1437-48.
Dharmawardhane, S. et al. (1997) "Localization of p21-activated kinase 1 (PAK1) to pinocytic vesicles and cortical actin structures in stimulated cells," J. Cell. Biol. 138, 1265-1278.
Erickson, J.W. et al. (1996) "Mammalian Cdc42 is a brefeldin A-sensitive component of the Golgi apparatus," J. Biol. Chem. 271, 26850-26854.
Erickson, J.W. et al. (1997) "Identification of an actin cytoskeleton complex that includes IQGAP and the Cdc42 GTPase," J. Biol. Chem. 272, 24443-24447.
Fukata, M. et al. (1997) "Regulation of cross-linking of actin filament by IQGAP1, a target for Cdc42," J. Biol. Chem. 272; 29579-29583.
Harden, N. et al. (1996) "A Drosophila homolog of the Rac- and Cdc42-activated serine/threonine kinase PAK is a potential focal adhesion and focal complex protein that colocalizes with dynamic actin structures," Mol. Cell. Biol. 16, 1896-1908.
Hillier, L. et al. (1995) yg22e03.r1 Soars infant brain 1NIB *Homo sapiens* cDNA clone IMAGE:32974 5' similar to SP:KPAK-RAT p35465, EST Database Accession No. R18825.
Joneson, T. et al. (1996) "RAC regulation of actin polymerization and proliferation by a pathway distinct from Jun kinase," Science 274, 1374-1376.
Kozma, R. et al. (1995) "The Ras-related protein Cdc42Hs and bradykinin promote formation of peripheral actin microspikes and filopedia in Swiss fibroblasts," Mol. Cell. Biol. 15, 1942-1952.
Kuroda, S. et al. (1996) "Identification of IQGAP as a putative target for the small GTPases, Cdc42 and Rac1," J. Bio. Chem. 271, 23363-23367.
Manser, E. et al. (1997) "Expression of constitutively active alpha-PAK reveals effects of the kinase on actin and focal complexes," Mol. Cell. Biol. 17, 1129-1143.
Melnik, M.M. (1997) Genbank Accession No. AF005046.
Pelech, S.L. (1996) "Kinase connections on the cellular intranet. Signalling Pathways," Curr. Biol. 6, 551-554.
Rana, A. et al. (1996) "The mixed lineage kinase SPRK phosphorylates and activates the stress-activated protein kinase activator SEK-1," J. Biol. Chem. 271, 19025-19028.
Sells, M.A. et al. (1997) "Human p21-activated kinase (Pak1) regulates actin organization in mammalian cells," Curr. Biol. 7, 202-210.

(Continued)

*Primary Examiner*—Hope A Robinson
(74) *Attorney, Agent, or Firm*—John P. White; Cooper & Dunham LLP

(57) ABSTRACT

This invention provides nucleic acids encoding human PAK5-related proteins, and provides the encoded proteins. This invention also provides vectors, cells and compositions. Finally, this invention provides methods of inducing and inhibiting various cellular processes using the instant nucleic acids and proteins.

16 Claims, 13 Drawing Sheets

OTHER PUBLICATIONS

Szczepanowska, J. et al. (1997) "Identification by mass spectrometry of the phosphorylated residue responsible for activation of the catalytic domain of myosin I heavy chain kinase, a member of the PAK/STE20 family," Proc. Natl. Acad. Sci. U.S.A. 94, 8503-8508.

Teramoto, H. et al. (1996) "Signaling from the small GTP-binding proteins Rac1 and Cdc42 to the c-Jun N-terminal kinase/stress-activated protein kinase pathway. A role for mixed lineage kinase 3/protein-tyrosine kinase 1, a novel member of the mixed lineage kinase family," J. Biol. Chem. 271, 27225-277228.

Van Aelst, L. and D'Souza-Schorey, C. (1997) "Rho GTPases and signaling networks," Genes Dev. 11; 2295-2322.

Westwick, J.K. et al. (1997) "Rac regulation of transformation, gene expression, and actin organization by multiple, PAK-Independent pathways," Mol. Cell. Biol. 17, 1324-1335.

Zhang, S. et al. (1995) "Rho family GTPases regulate p38 mitogen-activated protein kinase through the downstream mediator Pak1," J. Biol. Chem. 270, 23934-23936.

Database EMBL, Oct. 1, 2000, Watanabe, et al., "Serine/Threonine-protein kinase Pak 5" XP002164869, retrieved from EBI accession No. q9p286.

Database EMBL, Apr. 26, 2000, Watanabe, et al., "Pak, a novel group II PAK family kinase that is predominantly expressed in the brain" XP002411019, retrieved from EBI accession No. BAA94194.

Database EMBL, Apr. 26, 2000, Watanabe, et al., "Pak, a novel group II PAK family kinase that is predominantly expressed in the brain" XP002411020, retrieved from EBI accession No. AB040812.

Pandey, A. et al., "Cloning and characterization of PAK5, a novel member of mammalian p21-activated kinase-II subfamily that is predominantly expressed in brain", Oncogene, vol. 21, No. 24, May 30, 2002, pp. 3939-3948.

Jaffer, Z. et al., "p21-Activated kinases: three more join the Pak", International Journal of Biochemistry and Cell Biology, vol. 34, No. 7, 2002, pp. 713-717.

Dan, C. et al., "PAK5, a new brain-specific kinase, promotes neurite outgrowth in N1E-115 Cells", Molecular and Cellular Biology, vol. 22, No. 2, Jan. 2002, pp. 567-577.

Cau, J. et al., "A novel p21-activated kinase binds the actin and microtubule networks and induces microtubule stabilization", Journal of Cell Biology, vol. 155, No. 6, Dec. 10, 2001, pp. 1029-1042.

Daniels, R.H. et al., "Membrane targeting of p21-activated kinase 1 (PAK1) induces neurite outgrowth from PC12 cells", EMBO Journal, vol. 17, No. 3, Feb. 2, 1998, pp. 754-764.

Bagrodia, S. et al., "Pak to the future", Trends in Cell Biology, vol. 9, No. 9, Sep. 1999, pp. 350-355.

Xia, C. et al., "Regulation of the p21-activated kinase (PAK) by a human Gβ-like WD-repeat protein, hPIP1", Proceedings of the National Academy of Sciences of the United States of America, vol. 98, No. 11, May 22, 2001, pp. 6174-6179.

Aspenstrom, P. et al. (1996) Two GTPases, Cdc42 and Rac, bind directly to a protein implicated in the immunodeficiency disorder Wiskott-Aldrich syndrome. Curr. Biol. 6, 70-75 (Exhibit 9).

Bagrodia, S. et al. (1995) Cdc42 and PAK-mediated signaling leads to Jun kinase and p38 mitogen-activated protein kinase activation. J. Biol. Chem. 270, 27995-27998 (Exhibit 10).

Bashour, A.M. et al. (1997) IQGAP1, a Rac- and Cdc42-binding protein, directly binds and cross-links microfilaments. J. Cell. Biol. 137, 1555-1566 (Exhibit 11).

Benner, G.E. et al. (1995) Activation of an S6/H4 kinase (PAK 65) from human placenta by intramolecular and intermolecular autophosphorylation. J. Biol. Chem. 270, 21121-21128 (Exhibit 12).

Bershadsky, A., and Futerman, A. (1994) Disruption of the Golgi apparatus by brefeldin A blocks cell polarization and inhibits directed cell migration. Proc. Natl. Acad. Sci. U.S.A. 91, 5685-5689 (Exhibit 13).

Brown, J. et al. (1996) Human Ste20 homologue hPAK1 links GTPase to JNK MAP kinase pathway. Curr. Biol. 6, 598-605 (Exhibit 14).

Burbelo, P.D. et al. (1995) A conserved binding motif defines numerous candidate target proteins for both Cdc42 and Rac GTPases. J. Biol. Chem. 276, 29071-29074 (Exhibit 15).

Coso, O.A. et al. (1995) The small GTP-binding proteins Rac1 and Cdc42 regulate the activity of the JNK/SAPK signaling pathway. Cell 81, 1137-1146 (Exhibit 16).

Cvrckova, F. et al. (1995) Ste20-like protein kinases are required for normal localization of cell growth and for cytokinesis in budding yeast. Genes Dev. 9, 1817-1830 (Exhibit 17).

Dascher, C., and Balch, W.E. (1994) Dominant inhibitory mutants of ARF1 block endoplasmic reticulum to Golgi transport and trigger disassembly of the Golgi apparatus. J. Biol. Chem. 269, 1437-48 (Exhibit 18).

Dharmawardhane, S. et al. (1997) Localization of p21-activated kinase 1 (PAK1) to pinocytic vesicles and cortical actin structures in stimulated cells. J. Cell. Biol. 138, 1265-1278 (Exhibit 19).

Donaldson, J.G. et al. (1992) ABP-ribosylation factor, a small GTP-binding of the coatomer protein beta-COP to Glogi membranes. Proc. Natl. Acad. Sci. U.S.A. 89, 6408-6412 (Exhibit 20).

Donaldson, J.G. et al. (1992) Erefaldin A inhibits golgi membrane-catalysed exchange of guanine nucleotide into ARF protein. Nature 360, 350-352 (Exhibit 21).

Dutartre, H. et al. (1994) Cytokinesis arrest and redistribution of actin-cytoskeleton regulatory components in cells expressing the Fho GTPase CDC42HS. J. Cell. Sci. 109, 367-377 (Exhibit 22).

Erickson, J.W. et al. (1996) Kammalian Cdc42 is a brefeldin A-sensitive component of the Golgi apparatus. J. Biol. Chem. 271, 26850-26854 (Exhibit 23).

Erickson, J.W. et al. (1997) Identification of an actin cytoskeletal complex that includes IQGAP and the Cdc42 GTPase. J. Biol. Chem. 272, 24443-24447 (Exhibit 24).

Fukata, M. et al. (1997) Regulation of cross-linking of actin filament by IQGAP1, a target for Cdc42. J. Biol. Chem. 272, 29579-29583 (Exhibit 25).

Hanks, S.K. et al. (1989) The protein kinase family: conserved features and deduced phylogeny of the catalytic domains. Science 241, 42-52 (Exhibit 26).

Harden, N. et al. (1996) A Drosophila homolog of the Rac- and Cdc42- activated serine/threone kinase PAK is a potential focal adhesion and focal complex protein that colocalizes with dynamic actin structures. Mol. Cell. Biol. 16, 1896-1908 (Exhibit 27).

Hart, M.M. et al. (1996) IQGAP, a calmodulin-binding protein with a rasSAP- related domain, is a potential effector for cdc4Hs. EMBO J. 15, 2997-3005 (Exhibit 28).

Helms, J.B., and Fothman, J.E. (1992) Inhibition by brefeldin A of a golgi membrane enzyme that catalyses exchange of guanine nucleotide bound to ARF. Nature 360, 352-354 (Exhibit 29).

Hillier, L. et al. (1995) yg22eG3.r1 Soars infant brain 1NIB *Homo sapiens* cDNA clone IMAGE:32974 5' similar to SP:KPAK-RAT p35465, EST Catatse Accession No. R18825 (Exhibit 30).

Johnson, L. et al. (1996) Active and inactive protein kinases: structural basis for regulation. Cell 65, 149-158 (Exhibit 31).

Joneson, T. et al. (1996) RAC regulation of actin polymerization and proliferation by a pathway distinct from Jun kinase. Science 274, 1374-1379 (Exhibit 32).

Kozma, R. et al. (1995) The Ras-related protein Cdc42Hs and bradykinin promote formation of peripheral actin microspikes and filopodia in Swiss fibroblasts. Mol. Cell. Biol. 15, 1942-1952 (Exhibit 33).

Kuroda, S. et al. (1996) Identification of IQGAF as a putative target for the small GTPases, Cdc42 and Rac1. J. Bio. Chem. 271, 23363-23367 (Exhibit 34).

Lamarche, N. et al. (1996) Rac and Cdc42 induce actin polymerization and G1 cell cycle progression independently of p65PAK and the JNK/SAFK MAP 10 kinase cascade. Cell 87, 519-529 (Exhibit 35).

Manser, E. et al. (1993) A non-receptor tyrosine kinase that inhibits the GTPase activity of p21cdc42. Nature 363, 364-367 (Exhibit 36).

Manser, E. et al. (1994) A brain serine/threonine protein kinase activated by Cdc42 and Facl. Nature 367, 40-46 (Exhibit 37).

Manser, E. et al. (1997) Expression of constitutively active alpha-PAK reveals effects of the kinase on actin and focal complexes. Mol. Cell. Biol. 17, 1129-1143 (Exhibit 38).

Manser, E. et al. (1998) PAK kinases are directly coupled to the PIX family of nucleotide exchange factors. Mol. Cell. 1, 183-192 (Exhibit 39).

Marshall, C.J. (1994) Signal transduction. Hot lips and phosphorylation of protein kinases. Nature 367, 686 (Exhibit 40).

Martin, G.A. et al. (1995) A novel serine kinase activated by rac1/CDC42Hs-dependent autophosphorylation is related to PAK65 and STE20. EMBO J. 14, 1970-1979 (Exhibit 41).

Melnik, M.M. (1997) GenBank Accession No. AF005046 (Exhibit 42).

Minden, A. et al. (1994) Differential activation of ERK and JNK mitogen-activated protein kinases by Raf-1 and MEKK. Science 266, 1719-1733 (Exhibit 43).

Minden, A. et al. (1995) Selective activation of the JNK signaling cascade and c-Jun transcriptional activity by the small GTPases Rac and Cdc42Hs. Cell 81, 1147-1157 (Exhibit 44).

Nobes, C.D., and Hall, A. (1995) Bho, rac, and cdc42 GTPases regulate the assembly of multimolecular focal complexes associated with actin stress fibers, lamellipodia, filopodia. Cell 83, 53-62 (Exhibit 45).

Orci, L. et al. (1991) Brefelair. A, a drug that blocks secretion, prevents the assembly of non-clathrin-coated buds on *Golgi cisternae*. Cell 64, 1183-1195 (Exhibit 46)

Pelech, S.L. (1996) Kinase connections on the cellular intranet. Signalling pathways. Curr. Biol. 6, 551-554 (Exhibit 47).

Rana, A. et al. (1996) The mixed lineage kinase SPRK phosphorylates and activates the stress-activated protein kinase activator, SEK-1. J. Biol. Chem. 271, 19025-19026 (Exhibit 48).

Schekman, R., and Orci, L. (1996) Coat proteins and vesicle budding. Science 271, 1526-1533 (Exhibit 49).

Sells, M.A. et al. (1997) Humar. p21-activated kinase (Pak1) regulates actin organization in mammalian cells. Curr. Biol. 7, 202-210 (Exhibit 50).

Sells, M.A., and Cherrof, J. (1997) Emerging from the Pak: the p21-activated protein kinase family. Trends. Cell. Biol. 7, 166-167 (Exhibit 51).

Sigma catalog, Biochemicals and Organic Compounds for Research and Diagnostic Reagents, "Anonymous" ALA-VAL fragment, p. 64 (Exhibit 52).

Symons, M. et al. (1996) Wiskott-Aldrich syndrome protein, a novel effector for the GTPase CDC42Hs, is implicated in actin polymerization. Cell 84, 723-734 (Exhibit 53).

Szczepanowska, J. et al. (1997) Identification by mass spectrometry of the phosphorylated residue responsible for activation of the catalytic domain of myosin I heavy chain kinase, a member of the PAK/STE..0 family. Proc. Natl. Acad. Sci. U.S.A. 94, 8503-8508 (Exhibit 54).

Takebe, Y. et al. (1988) SR alpha promoter: an efficient and versatile mammalian cDNA expression system composed of the simian virus 40 early promoter and the F-U5 segment of human T-cell leukemia virus type 1 long terminal repeat. Mol. Cell. Biol. 8, 466-472 (Exhibit 55).

Teramoto, H. et al. (1996) Signaling from the small GTP-binding proteins Rac1 and Cdc42 to the c-Jun N-terminal kinase/stress-activated protein kinase pathway. A role for mixed lineage kinase 3/protein-tyrosine kinase 1, a novel member of the mixed lineage kinase family. J. Biol. Chem. 271, 27225-277228 (Exhibit 56).

Van Aelst, L. et al. (1996) Identification of a novel Rac1-interacting protein involved in membrane ruffling. EMBO J. 15, 3778-3786 (Exhibit 57).

Van Aelst, L., and D'Souza-Schorey, C. (1997) Bho GTPases and signaling networks. Genes Dev. 11, 2295-2322 (Exhibit 58).

Westwick, J.K. et al. (1997) Rac regulation cf transformation, gene expression, and actin organization by multiple, PAK-Independent pathways. Mol. Cell. Biol 17, 1324-1335 (Exhibit 59).

Zhang, C. J. et al. (1994) Expression of a dominant allele of human AFF1 inhibits membrane traffic in vivo. J. Cell. Biol. 124, 289-300 (Exhibit 60).

Chang, F. et al. (1994) Atomic structure of the MAP kinase ERK2 at 2.3 A resolution. Nature 367, 704-711 (Exhibit 61).

Chang, S. et al. (1995) Rhc family GTPases regulate p38 mitogen-activated protein kinase through the downstream mediator Pak1. J. Biol. Chem. 270, 23934-23936 (Exhibit 62).

International Search Report, Oct. 20, 2004 from International Searching Authority on International Application No. PCT/US02/41557.

Official Action issued Sep. 30, 2008 in connection with Japanese Patent Application No. 2003-558137, filed Jun. 28, 2004.

Abo, A., et al. (1998) "PAK4, a novel effector for Cdc42Hs, is implicated in the reorganization of the actin cytoskeleton and in the formation of filopodia", EMBO J. 17:6527-40.

* cited by examiner

```
1     ATGTTTGGAAGAAAAAGAAAAAGATTGAAATATCTGGCCCGTCCAACTTTGAACACAGGGTTCATACTGGGTTT
      M  F  G  K  K  K  K  K  I  E  I  S  G  P  S  N  F  E  H  R  V  H  T  G  F        25
76    GATCCACAAGAGCAGAAGTTTACCGGCCTTCCCCAGCAGTGGCACAGCCTGTTAGCAGATACGGCCAACAGGCCA
      D  P  Q  E  Q  K  F  T  G  L  P  Q  Q  W  H  S  L  L  A  D  T  A  N  R  P        50
151   AAGCCTATGGTGGACCCTTCATGCATCACACCCATCCAGCTGGCTCCTATGAAGACAATCGTTAGAGGAAACAAA
      K  P  M  V  D  P  S  C  I  T  P  I  Q  L  A  P  M  K  T  I  V  R  G  N  K        75
226   CCCTGCAAGGAAACCTCCATCAACGGCCTGCTAGAGGATTTTGACAACATCTCGGTGACTCGCTCCAACTCCCTA
      P  C  K  E  T  S  I  N  G  L  L  E  D  F  D  N  I  S  V  T  R  S  N  S  L        100
301   AGGAAAGAAAGCCCACCCACCCCAGATCAGGGAGCCTCCAGCCACGGTCCAGGCCACGCGGAAGAAAATGGCTTC
      R  K  E  S  P  P  T  P  D  Q  G  A  S  S  H  Q  P  G  H  A  E  E  N  G  F        125
376   ATCACCTTCTCCCAGTATTCCAGCGAATCCGATACTACTGCTGACTACACGACCGAAAAGTACAGGGAGAAGAGT
      I  T  F  S  Q  Y  S  S  E  S  D  T  T  A  D  Y  T  T  E  K  Y  R  E  K  S        150
451   CTCTATGGAGATGATCTGGGTCCGTATTATAGAGGCAGCCACGCAGCCAAGCAAAATGGGCACGTAATGAAAATG
      L  Y  G  D  D  L  G  P  Y  Y  R  G  S  H  A  A  K  Q  N  G  H  V  M  K  M        175
526   AAGCACGGGGAGGCCTACTATTCTGAGGTGAAGCCTTTGAAATCCGATTTTGCCAGATTTTCTGCCGATTATCAC
      K  H  G  E  A  Y  Y  S  E  V  K  P  L  K  S  D  F  A  R  F  S  A  D  Y  H        200
601   TCACATTTGGACTCACTGAGCAAACCAAGTGAATACAGTGACCTCAAGTGGGAGTATCAGAGAGCCTCGAGTAGC
      S  H  L  D  S  L  S  K  P  S  E  Y  S  D  L  K  W  E  Y  Q  R  A  S  S  S        225
676   TCCCCTCTGGATTATTCATTCCAATTCACACCTTCTAGAACTGCAGGGACCAGCGGGTGCTCCAGGGAGAGCCTG
      S  P  L  D  Y  S  F  Q  F  T  P  S  R  T  A  G  T  S  G  C  S  R  E  S  L        250
751   GCGTACAGTGAAAGTGAATGGGGACCCAGCCTGGATGACTATGACAGGAGGCCAAAGTCTTCGTACCTGAATCAG
      A  Y  S  E  S  E  W  G  P  S  L  D  D  Y  D  R  R  P  K  S  S  Y  L  N  Q        275
826   ACAAGCCCTCAGCCCACCATGCGGCAGAGGTCCAGGTCAGGCTCGGGACTCCAGGAACCGATGATGCCATTTGGA
      T  S  P  Q  P  T  M  R  Q  R  S  R  S  G  S  G  L  Q  E  P  M  M  P  F  G        300
901   GCAAGTGCATTTAAAACCCATCCCCAAGGACACTCCTACAACTCCTACACCTACCCTCGCTTGTCCGAGCCCACA
      A  S  A  F  K  T  H  P  Q  G  H  S  Y  N  S  Y  T  Y  P  R  L  S  E  P  T        325
976   ATGTGCATTCCAAAGGTGGATTACGATCGAGCACAGATGGTCCTCAGCCCTCCACTGTCAGGGTCTGACACCTAC
      M  C  I  P  K  V  D  Y  D  R  A  Q  M  V  L  S  P  P  L  S  G  S  D  T  Y        350
1051  CCCAGGGGCCCTGCCAAACTACCTCAAAGTCAAAGCAAATCGGGCTATTCCTCAAGCAGTCACCAGTACCCGTCT
      P  R  G  P  A  K  L  P  Q  S  Q  S  K  S  G  Y  S  S  S  S  H  Q  Y  P  S        375
1126  GGGTACCACAAAGCCACCTTGTACCATCACCCCTCCCTGCAGAGCAGTTCGCAGTACATCTCCACGGCTTCCTAC
      G  Y  H  K  A  T  L  Y  H  H  P  S  L  Q  S  S  S  Q  Y  I  S  T  A  S  Y        400
1201  CTGAGCTCCCTCAGCCTCTCATCCAGCACCTACCCGCCCCAGCTGGGGCTCCTCCTCCGACCAGCAGCCCTCC
      L  S  S  L  S  L  S  S  S  T  Y  P  P  P  S  W  G  S  S  S  D  Q  Q  P  S        425
1276  AGGGTGTCCCATGAACAGTTTCGGGCGGCCCTGCAGCTGGTGGTCAGCCCAGGAGACCCCAGGGAATACTTGGCC
      R  V  S  H  E  Q  F  R  A  A  L  Q  L  V  V  S  P  G  D  P  R  E  Y  L  A        450
1351  AACTTTATCAAAATCGGGGAAGGCTCAACCGGCATCGTATGCATCGCCACCGAGAAACACACAGGGAAACAAGTT
      N  F  I  K  I  G  E  G  S  T  G  I  V  C  I  A  T  E  K  H  T  G  K  Q  V        475
1426  GCAGTGAAGAAAATGGACCTCCGGAAGCAACAGAGACGAGAACTGCTTTTCAATGAGGTCGTGATCATGCGGGAT
      A  V  K  K  M  D  L  R  K  Q  Q  R  R  E  L  L  F  N  E  V  V  I  M  R  D        500
1501  TACCACCATGACAATGTGGTTGACATGTACAGCAGCTACCTTGTCGGCGATGAGCTCTGGGTGGTCATGGAGTTT
      Y  H  H  D  N  V  V  D  M  Y  S  S  Y  L  V  G  D  E  L  W  V  V  M  E  F        525
1576  CTAGAAGGTGGTGCCTTGACAGACATTGTGACTCACACCAGAATGAATGAAGAGCAGATAGCTACTGTCTGCCTG
      L  E  G  G  A  L  T  D  I  V  T  H  T  R  M  N  E  E  Q  I  A  T  V  C  L        550
1651  TCAGTTCTGAGAGCTCTCTCCTACCTTCATAACCAAGGAGTGATTCACAGGGACATAAAAAGTGACTCCATCCTC
      S  V  L  R  A  L  S  Y  L  H  N  Q  G  V  I  H  R  D  I  K  S  D  S  I  L        575
1726  CTGACAAGCGATGGCCGGATAAAGTTGTCTGATTTTGGTTTCTGTGCTCAAGTTTCCAAAGAGGTGCCGAAGAGG
      L  T  S  D  G  R  I  K  L  S  D  F  G  F  C  A  Q  V  S  K  E  V  P  K  R        600
1801  AAATCATTGGTTGGCACTCCCTACTGGATGGCCCCTGAGGTGATTTCTAGGCTACCTTATGGGACAGAGGTGGAC
      K  S  L  V  G  T  P  Y  W  M  A  P  E  V  I  S  R  L  P  Y  G  T  E  V  D        625
1876  ATCTGGTCCCTCGGGATCATGGTGATAGAAATGATTGATGGCGAGCCCCCTACTTCAATGAGCCTCCCCTCCAG
      I  W  S  L  G  I  M  V  I  E  M  I  D  G  E  P  P  Y  F  N  E  P  P  L  Q        650
1951  GCCGATGCGGAGGATCCGGGACAGTTTACCTCCAAGAGTGAAGGACCTACACAAGGTTTCTTCAGTGCTCCGGGA
      A  M  R  R  I  R  D  S  L  P  P  R  V  K  D  L  H  K  V  S  S  V  L  R  G        675
2026  TTCCTAGACTTGATGTTGGTGAGGGAGCCCTCTCAGAGAGCAACAGCCCAGGAACTCCTCGGACATCCATTCTTA
      F  L  D  L  M  L  V  R  E  P  S  Q  R  A  T  A  Q  E  L  L  G  H  P  F  L        700
2101  AAACTAGCAGGTCCACCCGTCTTGCATCGTCCCCCTCATGAGACAATACAGGCATCACTGA
      K  L  A  G  P  P  S  C  I  V  P  L  M  R  Q  Y  R  H  H  •                        719
```

```
PAK5  MFGKKKKK-IEISGPSNFEHRVHTGFDPQEQKFTGLPQGWHSLLADTANRPKPMVDPSCI  59
PAK4  MFGKRKKR-VEISAPSNFEHRVHTGFDQHEQKFTGLPRQWQSLIEESARRPKPLVDPACI  59
PAK6  MFRKKKKKRPEISAPQNFQHRVHTSFDPKSGKFVGLPPQWQN-ILDILRRPKPVVDPSRI  59

PAK5  IPIQLAPMKTIVRGNKPCKETSINGLIEDTDNISVTRSNSLRKESPPTPDQGASSHGPCH  119
PAK4  TSIQPGAPKTIVRGSKGAKDGALTLLIDEFENMSVTRSNSLRRDSPPPPARAR------  112
PAK6  IRVQLQPMKTVVRGSAMPVDGYISGLLNDIQKLSVISSNTLRGRSPTSRRRAQSLGLLG-  118

PAK5  AEENGFITFSQYSSESDTIADYTTEKYREKSLYGDDLDPYYRGSHAAKQNGHVMKMKHGE  179
PAK4  -QENGMP------EEPATIARGGPGKAGS----------RGRFAG------------  140
PAK6  -DEHWATDPDMYLQSPQSERTDPHGLYLSCN---------GGTPAG----------HKQ  157

PAK5  AYYSEVKPLKSDFARFSADYHSHLDSLSKPSEYSDLKWEYQRASSSSPLDYSFDITPSRT  239
PAK4  ------------------------------------------------HSEA  144
PAK6  MPWPEPQSPRVLPNGLAAKAQSLG-----PAEFQG------ASQRCLQLGACLQSSPPGA  206

PAK5  AGTSGCSKESLAYSESEWGPSLDDYDRRPKSSYL--------NQTSPQPTMR-----QRS  286
PAK4  GGGSGDRRR--------AGP-----EKRPKSSRE--------GSGGPQESSRD----KRP  179
PAK6  SPPTGTNRHG--MKAAKHGSE----EARPQSCLVGSATGRPGGEGSPSPKTRESSLKRAL  260

PAK5  RSGSGLQEPM-MPFGASAFKTHPQGHSYNSYTYPRLSEPTMCIPKVDYDRAQHVLSPPLS  345
PAK4  LSGPDVGTP--QPAGLASGAKLAAGRPFNTVPRADTDHPSRGAQGEPHDVAPNGPS----  233
PAK6  FRSMFLSTAATAPPSSSKPGPPPQSKPNSSFRPPQKDNPPSLVAKAQSLPSDQPVG----  316

PAK5  GSDTYPRGPAKLPQSQSKSGYSSSHQYPSGYHKATLYHHPSLQSSSQYISTASYLSSLS  405
PAK4  ------AGGLAIPQS-----SSSSSRPPTRARGAPSPGVLGPHASEPQLAPP----ACT  277
PAK6  -----TFSPLTTSDT-----SSPQKSLRTAPATGQLPGRSSPAGSPRTWHAQ--ISTSN  363

I
PAK5  LSSSTYPPPSWGSSSDQQPSRVSHEQFRAALQLVVSPGDPREYLANFIKIGEGSTGIVCI  465
PAK4  PAAPAVPGPPGPRSPQREPQRVSHEQFRAALQLVVDPGDPRSYLDNFIKIGEGSTGIVCI  337
PAK6  LYLPQDPTVAKGALAGEDTGVVTHEQFKAALRHVVDQGDPRLLLDSYVKIGEGSTGIVCL  423

II             III          IV
PAK5  ATEKHTGKQVAVKKMDLRKQQRRELLFNEVVIMRDYHHDNVVQMYSSYLVGDELWVVMEF  525
PAK4  ATVRSSGKLVAVKKMDLRKQQRRELLFNEVVIMRDYHHENVVEMYNSYLVGDELWVVMEF  397
PAK6  AREKHSGRQVAVKMMDLRKQQRRELLFNEVVIMRDYQHFNVVEMYKSYLVGEELWVLMEF  483

V              VIA            VIB
PAK5  LEGGALTDIVTHTRMNEEQIATVCLSVLRALSYLHNQGVIHRDIKSDSILLTSDGRIKLS  585
PAK4  LEGGALTDIVTHTRMNEEQIAAVCLAVLQALSVLHAQGVIHRDIKSDSILLTHDGRVKLS  457
PAK6  LQGGALTDIVSQVRLNEEQIATVCEAVLQAEAYLHAQGVIHRDIKSDSILLTLDGRVKLS  543

VII                VIII                IX
PAK5  DFGFCAQVSKEVPKRKSLVGTPYWMAPEVISRLPYGTEVDIWSLGIMVIEMIDGEPPYFN  645
PAK4  DFGFCAQVSKEVPRRKSLVGTPYWMAPELISRLPYGPEVDIWSLGIMVIEMVDGEPPYFN  517
PAK6  DFGFCAQISKDVPKRKSLVGTPYWMAPEVISRSLYATEVDIWSLGIMVIEMVDGEPPYFS  603

X                            XI
PAK5  EPPLQAMRRIRDSLPPRVKDLHKVSSVLRGFLDLMLVREPSQRATAQELLGHPFLKLAGP  705
PAK4  EPPLKAMKMIRDNLPPRLKNLHKVSPSLKGFLDRLLVRDPAQRATAAELLKHPFLAKAGP  577
PAK6  DSPVQAMKRLRDSPPPKLKNSHKVSPVLRDFLERMLVRDPAQERATAQELLDHPFILQTGL  663

PAK5  PSCIVPLMRQYRHH----  719
PAK4  PASIVPLMRQNRTR----  591
PAK6  PECLVPLIQLYRKQTSTC  681
```

Figure 1D

```
atgtttggga agaaaaagaa aaagatcgaa atatctggcc catccaactt tgaacacagg    60
gttcatactg gatttgatcc acaagagcag aagtttactg gccttcccca gcagtggcac   120
agcctgttag cagacacagc caacaggccc aagcccatgg tggacccatc atgcatcaca   180
cccatacagc tggctccat gaagacaatc gtcagaggaa ataaatcctg caaggaaacc    240
tctatcaatg gtctgctaga ggattttgac aacatctccg tgactcgctc caactctcta   300
aggaaagaaa gcccacccac cccagatcag ggagcagcta gccgcattca aggccactcg   360
gaagagaacg gcttcatcac tttctcacaa tattccagtg aatccgatac gactgcggac   420
tacacaactg aaaagtacag agacaggagt ctctatggag atgacctgga tctgtactat   480
aaaagcagcc atgcagccaa gcaaaatggg catgccatga agatgaaaca tggagacgct   540
tactaccctg agatgaagtc tttgaaaacc gacctggccg gattccctgt cgactatcac   600
acccacttgg actctctgag aaaatcaagt gaatatggtg accttaggtg ggattatcag   660
agagcctcta gtagctcccc tctggactac tcattccagc tcacgccttc tagaactgca   720
gggaccagca ggtgctccaa ggagagtctg gcatacagtg aaagtgattg gggacccagc   780
ctggatgact atgacaggag gccaaaatca tcatacctgc atcagacgag ccctcagcca   840
gccatgcgcc agagatccaa gtccggctca gggcttcagg aacccatgat gccatttgga   900
gcaagtgcat ttaaaactca tcctcaagga cactcgtaca actcctacac ctaccctcga   960
ttgtccgagc ccacaatgtg cattccaaag gtggattacg atcgagcaca gatggtcttc  1020
agtcctccac tgtcagggtc cgacacttac cccagaggcc ccaccaaact acctcaaagt  1080
caaagcaaag caggctactc ttcaggcagc caccagtacc cttctgggta ccacaaagca  1140
tctctatacc accatccatc cctgcaaacc agttctcagt acatctccac cgcttcttac  1200
ttaagctctc tcagtatctc ctcgagcacc taccctccac ctagctgggg ctcctcctca  1260
gaccagcagc cctcaagggt atcccatgaa caattccgag ctgccctgca actggtggtc  1320
agcccaggag accccaggga atatttggat aactttatta aaatcggaga agggtcgaca  1380
ggcatcgtgt gcattgcaac agaaaaacac acaggcaagc aagtggcaat gaagaaaatg  1440
gacctccgaa agcagcagag acgggaactc ctttttaatg aggtcgtgat aatgcgtgat  1500
taccaccatg acaacgtagt tgacatgtac aacagctacc ttgttggaga tgagctctgg  1560
gtggtcatgg agttctctaga aggtggtgcc ttgacagaca ttgtcactca taccagaatg  1620
aatgaagagc agatagctac tgtctgcctg tcagttctga agctctgtc ctaccttcat   1680
aaccaaggag tgattcacag ggacataaag agtgactcca ttcttctgac aagcgatggc  1740
cggataaagt tatctgactt tggtttctgt gctcaagttt ccaaagaggt gccaagagag  1800
aagtcactgg tgggtacccc atactggatg gcacctgagg tgatttccag gctaccttat  1860
gggacagagg tggacatctg gtccctcggg ataatggtga tagagatgat tgatggggag  1920
ccccccctatt tcaatgagcc tcctctgcag gccatgagga ggatccggga cagtttacct  1980
ccaagagtga aggacctaca caaggtttct tccatgctcc gaggattcct agatcttatg  2040
```

Figure 1E ttggtgaggg agccctctcg aagagccaca gctcaagaac tccttggaca tccattctta    2100
aaattggcag gtccaccatc ttgcattgtt cctctcatga gacaatacag acatcactga    2160

Met Phe Gly Lys Lys Lys Lys Ile Glu Ile Ser Gly Pro Ser Asn
1               5               10              15

Phe Glu His Arg Val His Thr Gly Phe Asp Pro Gln Glu Gln Lys Phe
            20              25              30

Thr Gly Leu Pro Gln Gln Trp His Ser Leu Leu Ala Asp Thr Ala Asn
        35              40              45

Arg Pro Lys Pro Met Val Asp Pro Ser Cys Ile Thr Pro Ile Gln Leu
50              55              60

Ala Pro Met Lys Thr Ile Val Arg Gly Asn Lys Ser Cys Lys Glu Thr
65              70              75              80

Ser Ile Asn Gly Leu Leu Glu Asp Phe Asp Asn Ile Ser Val Thr Arg
            85              90              95

Ser Asn Ser Leu Arg Lys Glu Ser Pro Pro Thr Pro Asp Gln Gly Ala
            100             105             110

Ala Ser Arg Ile Gln Gly His Ser Glu Glu Asn Gly Phe Ile Thr Phe
            115             120             125

Ser Gln Tyr Ser Ser Glu Ser Asp Thr Thr Ala Asp Tyr Thr Thr Glu
            130             135             140

Lys Tyr Arg Asp Arg Ser Leu Tyr Gly Asp Asp Leu Asp Leu Tyr Tyr
145             150             155             160

Lys Ser Ser His Ala Ala Lys Gln Asn Gly His Ala Met Lys Met Lys
            165             170             175

His Gly Asp Ala Tyr Tyr Pro Glu Met Lys Ser Leu Lys Thr Asp Leu
            180             185             190

Ala Gly Phe Pro Val Asp Tyr His Thr His Leu Asp Ser Leu Arg Lys
            195             200             205

Ser Ser Glu Tyr Gly Asp Leu Arg Trp Asp Tyr Gln Arg Ala Ser Ser
210             215             220

Figure 1F

```
Ser Ser Pro Leu Asp Tyr Ser Phe Gln Leu Thr Pro Ser Arg Thr Ala
225             230             235             240

Gly Thr Ser Arg Cys Ser Lys Glu Ser Leu Ala Tyr Ser Glu Ser Asp
            245             250             255

Trp Gly Pro Ser Leu Asp Asp Tyr Asp Arg Arg Pro Lys Ser Ser Tyr
            260             265             270

Leu His Gln Thr Ser Pro Gln Pro Ala Met Arg Gln Arg Ser Lys Ser
            275             280             285

Gly Ser Gly Leu Gln Glu Pro Met Met Pro Phe Gly Ala Ser Ala Phe
    290             295             300

Lys Thr His Pro Gln Gly His Ser Tyr Asn Ser Tyr Thr Tyr Pro Arg
305             310             315             320

Leu Ser Glu Pro Thr Met Cys Ile Pro Lys Val Asp Tyr Asp Arg Ala
                325             330             335

Gln Met Val Phe Ser Pro Pro Leu Ser Gly Ser Asp Thr Tyr Pro Arg
            340             345             350

Gly Pro Thr Lys Leu Pro Gln Ser Gln Ser Lys Ala Gly Tyr Ser Ser
            355             360             365

Gly Ser His Gln Tyr Pro Ser Gly Tyr His Lys Ala Ser Leu Tyr His
    370             375             380

His Pro Ser Leu Gln Thr Ser Ser Gln Tyr Ile Ser Thr Ala Ser Tyr
385             390             395             400

Leu Ser Ser Leu Ser Ile Ser Ser Ser Thr Tyr Pro Pro Pro Ser Trp
            405             410             415

Gly Ser Ser Ser Asp Gln Gln Pro Ser Arg Val Ser His Glu Gln Phe
            420             425             430

Arg Ala Ala Leu Gln Leu Val Val Ser Pro Gly Asp Pro Arg Glu Tyr
            435             440             445

Leu Asp Asn Phe Ile Lys Ile Gly Glu Gly Ser Thr Gly Ile Val Cys
    450             455             460

Ile Ala Thr Glu Lys His Thr Gly Lys Gln Val Ala Val Lys Lys Met
465             470             475             480

Asp Leu Arg Lys Gln Gln Arg Arg Glu Leu Leu Phe Asn Glu Val Val
            485             490             495
```

Figure 1G

```
Ile Met Arg Asp Tyr His His Asp Asn Val Val Asp Met Tyr Asn Ser
        500             505                 510

Tyr Leu Val Gly Asp Glu Leu Trp Val Val Met Glu Phe Leu Glu Gly
        515             520                 525

Gly Ala Leu Thr Asp Ile Val Thr His Thr Arg Met Asn Glu Glu Gln
    530             535                 540

Ile Ala Thr Val Cys Leu Ser Val Leu Lys Ala Leu Ser Tyr Leu His
545             550                 555                     560

Asn Gln Gly Val Ile His Arg Asp Ile Lys Ser Asp Ser Ile Leu Leu
            565                 570                 575

Thr Ser Asp Gly Arg Ile Lys Leu Ser Asp Phe Gly Phe Cys Ala Gln
            580                 585                 590

Val Ser Lys Glu Val Pro Lys Arg Lys Ser Leu Val Gly Thr Pro Tyr
        595                 600                 605

Trp Met Ala Pro Glu Val Ile Ser Arg Leu Pro Tyr Gly Thr Glu Val
    610                 615                 620

Asp Ile Trp Ser Leu Gly Ile Met Val Ile Glu Met Ile Asp Gly Glu
625                 630                 635                 640

Pro Pro Tyr Phe Asn Glu Pro Pro Leu Gln Ala Met Arg Arg Ile Arg
                645                 650                 655

Asp Ser Leu Pro Pro Arg Val Lys Asp Leu His Lys Val Ser Ser Met
            660                 665                 670

Leu Arg Gly Phe Leu Asp Leu Met Leu Val Arg Glu Pro Ser Gln Arg
        675                 680                 685

Ala Thr Ala Gln Glu Leu Leu Gly His Pro Phe Leu Lys Leu Ala Gly
    690                 695                 700

Pro Pro Ser Cys Ile Val Pro Leu Met Arg Gln Tyr Arg His His
705
```

PAK5-RELATED COMPOSITIONS AND METHODS

This application claims the benefit of U.S. Provisional Application 60/343,972, filed Dec. 28, 2001, the contents of which are incorporated herein by reference.

The invention disclosed herein was made with United States government support under grant number ROI CA 76342 from the National Institutes of Health. Accordingly, the United States government has certain rights in this invention.

Throughout this application, various references are cited. Disclosure of these references in their entirety is hereby incorporated by reference into this application to more fully describe the state of the art to which this invention pertains.

BACKGROUND OF THE INVENTION

The Rho family GTPases, including Cdc42, Rac, and Rho, were first identified as proteins that have key roles in regulating the organization of the actin cytoskeleton in mammalian fibroblasts (18, 35, 37, 38). Microinjection of activated Cdc42 into fibroblasts causes the induction of filopodia, while activated Rac leads to lamellipodia formation, and activated Rho causes the formation of stress fibers. Both Cdc42Hs and Rac have also been shown to have a role in the dissolution of stress fibers (10, 18, 26), which may reflect an antagonism between these two GTPases and Rho (19, 39).

While they were initially characterized in fibroblasts, the Rho GTPases have also been shown to regulate the morphologies of other types of cells. For example, the Rho GTPases have been shown to have important roles in the regulation of neurite outgrowth in C. elegans, drosophila, chick, and mammalian primary neurons and cell lines (5, 8, 14, 19, 22, 25, 47, 53). This is probably due, at least in part, to the fact that filopodia and lamellipodia play key roles in the elongation of neurites (24). Previous studies have indicated that neurotrophic factors, such as NGF, BDGF, NT-3, NT-4, and chemoattractants such as netrin-1, can induce neurite outgrowth or regulate axon guidance (3, 45).

In mammalian neuronal cell lines, Cdc42 and Rac appear to act antagonistically with Rho. Introduction of constitutively active mutants of Cdc42 and Rac into N1E-115 neuroblastoma cells leads to the formation of neurites (40, 51) and the production of filopodia and lamellipodia in developing growth cones (19), while introduction of dominant negative mutants of Cdc42 and Rac inhibits neurite outgrowth in N1E-115 cells and PC12cells (8, 19, 40, 51). In contrast, activated RhoAV14 causes neurite retraction in PC12 cells and N1E-115 cells, while inhibition of RhoA stimulates the production of neurites in N1E-115 cells (11, 19, 49-51). These results suggest that inactivation of RhoA actually leads to the activation of Cdc42 and Rac, thus leading to the production of neurites (19). Consistent with this, N1E-115 cells form neurites when they are grown in the absence of serum, but not when they are grown in the presence of serum. This is presumably because components in serum, especially LPA, activate Rho, which in turn blocks the production of neurites in response to Cdc42 and Rac (19).

While Cdc42 and Rac clearly have important roles in regulating morphological changes that control growth cone formation and neurite outgrowth, the mechanisms by which the GTPases operate in neuronal cells are still not entirely understood. The identification and characterization of molecular targets for the Rho GTPases is an important step in determining how they control cell morphology in both neuronal cells and non-neuronal cells.

Members of the mammalian p21 activated kinase ("PAK") family of serine/threonine kinases constitute a family of kinases that bind to Rac and Cdc42, but not Rho (for review see (7, 17, 43)). The PAK family members can be placed into two categories based on their amino acid sequences. The first category includes human PAK1 and PAK2 and mouse PAK3. Each of these protein kinases has a carboxyl terminal kinase domain and an amino terminal regulatory domain. Within the regulatory domain is a GTPase binding domain ("GBD") that binds to activated Cdc42 and Rac. The regulatory domain also contains two to three proline-rich regions that bind to SH3 domain-containing proteins including the adaptor protein Nck and the exchange factor PIX (7), and a motif that can bind to G protein βγ subunits (7). The members of this family are all quite similar in sequence, exhibiting 73% overall sequence identity and approximately 92% sequence identity within the kinase and GBD domains (43). Members of this subfamily of PAKs are thought to have important roles in regulating cell morphology and cytoskeletal organization, although they may not specifically mediate cytoskeletal effects that are triggered by Cdc42 and Rac. (13, 21, 44, 46).

PAK4 is the first PAK family member to be identified as belonging to a second category of PAKs based on its sequence (1). PAK4 contains an amino terminal GBD and a carboxyl terminal kinase domain, but it does not bind to PIX or Nck and it does not have a G protein βγ-binding motif (1). Furthermore, the GBD and kinase domains of PAK4 have only approximately 50% identity with those of the other PAKs, and the regulatory domain of PAK4 outside of the GBD is completely different from the other PAKs (1). Unlike other PAKs, PAK4 was shown to be a link between Cdc42 and filopodia formation (1). In addition to filopodia formation, PAK4 may also have other functions. For example, a constitutively active PAK4 mutant also leads to the dissolution of stress fibers and focal adhesions, most likely by inhibiting the activity of RhoA (36).

SUMMARY OF THE INVENTION

This invention provides an isolated nucleic acid comprising a sequence encoding a mammalian PAK5 domain, with the proviso that the nucleic acid does not encode full-length human PAK5.

This invention also provides a nucleic acid comprising a sequence encoding a mammalian PAK5 GTPase-binding domain and a mammalian PAK5 regulatory domain, but not a mammalian PAK5 kinase domain.

This invention further provides a nucleic acid comprising a sequence encoding a mammalian PAK5 GTPase-binding domain and a mammalian PAK5 kinase domain, but not a mammalian PAK5 regulatory domain.

This invention further provides a nucleic acid comprising a sequence encoding a mammalian PAK5 regulatory domain and a mammalian PAK5 kinase domain, but not a mammalian PAK5 GTPase-binding domain.

This invention further provides an isolated nucleic acid which specifically hybridizes to nucleic acid encoding a mammalian PAK5.

This invention further provides a nucleic acid comprising a mammalian PAK5-encoding sequence operatively linked to an exogenous regulatory element.

This invention further provides a nucleic acid comprising a mammalian PAK5-encoding sequence operatively linked to an endogenous regulatory element.

This invention further provides a vector which comprises (a) one of the instant protein-encoding nucleic acids or (b) a nucleic acid encoding the instant nucleic acid which hybridizes thereto.

This invention further provides a cell comprising one of the instant regulatory element-linked nucleic acids.

This invention further provides proteins encoded by each of the instant nucleic acids.

This invention further provides compositions, each composition comprising a pharmaceutically acceptable carrier together with one of the instant nucleic acids or one of the instant proteins.

This invention further provides methods for regulating cells using the instant nucleic acids or proteins as appropriate. These methods include methods of inducing and inhibiting protrusion formation by a mammalian cell, causing cytoskeletal reorganization in a mammalian cell, inducing and inhibiting ruffle formation on a mammalian cell, inducing and inhibiting migration of a mammalian cell, and inducing and inhibiting proliferation of a mammalian cell.

This invention further provides a method of inhibiting the transcription of a mammalian PAK5-encoding DNA molecule using one of the instant nucleic acids.

This invention further provides a method of inhibiting the translation of a mammalian PAK5-encoding mRNA molecule using one of the instant nucleic acid molecules.

This invention further provides a method of increasing neuronal outgrowth in a subject comprising administering to the subject one of certain instant compositions as appropriate, in an amount effective to increase neuronal outgrowth in the subject.

This invention still further provides a method of inhibiting neuronal outgrowth in a subject comprising administering to the subject one of certain instant compositions as appropriate, in an amount effective to inhibit the subject's neuronal outgrowth.

This invention further provides a method of determining whether a mammalian cell's reduced ability to form protrusions is due to blockage of signal transduction either upstream or at the level of PAK5, which comprises: (a) introducing PAK5 into the cell; and (b) determining whether its number of protrusions increases, such increase indicating that the cell's reduced ability to form protrusions is due to blockage of signal transduction either upstream or at the level of PAK5.

Finally, this invention provides a non-human transgenic mammal whose somatic cells lack PAK5-encoding DNA.

The nucleic acid (SEQ. ID. NO:3) and amino acid (SEQ. ID. NO:4) sequences of human PAK5 are shown. Underlined regions of the amino acid sequence correspond to the GBD domain (amino acids 10-30) and the kinase domain (amino acids 452-702)

FIG. 1B

Multiple sequence alignment of the PAK5 amino acid sequence (SEQ. ID. NO:4) with the amino acid sequences of PAK4 (SEQ. ID. NO:7) and PAK6 (SEQ. ID. NO:8).

FIG. 1C

A human multiple tissue mRNA Northern blot was probed with cDNA containing part of the kinase domain of PAK5. A band of about 5.5 kb is indicated.

FIG. 1D-1G

The nucleic acid (SEQ. ID. NO:1) and amino acid (SEQ. ID. NO:2) sequences of mouse PAK5 are shown.

FIG. 2

PAK4 and PAK5 interact with activated Rac and Cdc42. 293 cells were transfected with equal amounts of expression vectors, encoding the following Myc-tagged proteins: wild type PAK4 (Myc-PAK4), wild type PAK5 (Myc-PAK5), or PAK5ΔGBD. After transient expression, the Myc-tagged proteins were immunoprecipitated from whole cell lysates using a mouse anti-Myc antibody and protein A sepharose. The immunocomplexes were separated by SDS-PAGE and transferred to a PVDF membrane. The membranes were then probed with purified RhoV14, Rac1V12 or Cdc42V12, as indicated. The GTPases were pre-loaded with [γ-$^{32}$P] GTP as described in the Materials and Methods. A portion of the lysate was used for Western blot analysis (WB) with an anti-Myc antibody to measure the amount of each transfected protein in the lysates.

Figures 3A, 3B:
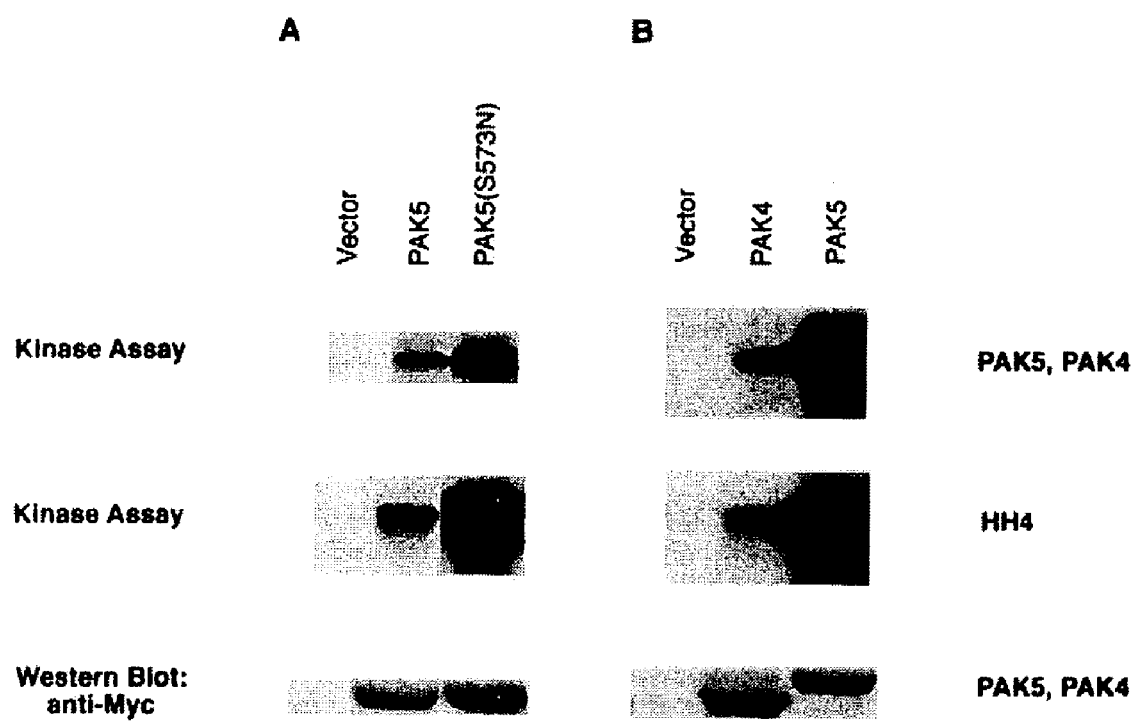

FIGS. 3A and 3B

PAK5 autophosphorylates and phosphorylates histone H4 (HH4). 293 cells were transfected with equal amounts of either GFP vector or expression vectors containing one of the following Myc-tagged proteins: PAK4, PAK5, or PAK5 (S573N). After transient expression, the amounts of Myc-tagged proteins were normalized by Western blots probed with a mouse anti-Myc antibody. Approximately equal amounts of Myc-PAK4, Myc-PAK5, and Myc-PAK5 (S573N) were immunoprecipitated from whole cell lysates using a mouse anti-Myc antibody and protein A sepharose. The immunocomplexes were then incubated with histone H4 and [γ-$^{32}$P] ATP in in vitro kinase buffer. Substrate phosphorylation and autophosphorylation were analyzed after SDS-PAGE (15% gel) and autoradiography. Both the autophosphorylation of PAK4, PAK5, PAK5 (S573N) and the phosphorylation of Histone H4 are indicated. In Panel A, the gel was exposed for 15 min, and in Panel B, the gel was exposed for 2 hr. Western blots showing expression of Myc-PAK5 and Myc-PAK4 are shown in the bottom panel (10% gel).

FIG. 4

PAK5 activates the JNK pathway. 293 cells were transfected with either empty vector, or 5 µg expression vector containing HA-tagged JNK (HA-JNK) either alone or with increasing doses of expression vectors containing Myc-tagged PAK5 (1, 3, and 5 µg), or expression vectors containing Rac2L61 (2.5 µg), or MEKK1Δ (2.5 µg). After transient expression, cells were lysed, and the amount of HA-JNK was normalized by Western blots probed with a mouse anti-HA antibody. Equal amounts of HA-JNK were then immunoprecipitated from whole cell lysates using a mouse anti-HA antibody and protein A sepharose. The immunoprecipitates were then incubated with recombinant GST-c-Jun in the presence of [γ-$^{32}$P] ATP in in vitro kinase buffer. Substrate phosphorylation was analyzed after SDS-PAGE and autoradiography. The phosphorylation of GST-c-Jun is indicated. The numbers indicate the fold of activation of JNK by PAK5, Rac2L61 and MEKK1Δ quantitated by phosphorimager analysis.

FIG. 5A

PAK5 induces neurite outgrowth and filopodia. Expression vectors containing EGFP (control), PAK5, PAK5 (S573N), PAK4, PAK4 (S445N) or PAK1 (T423E) were transfected into N1E-115 cells. Vectors containing PAK4 and PAK5 were either co-transfected with an EGFP vector at a 1:3 (EGFP:PAK5) ratio or expressed as EGFP fusions, with similar results. PAK1 (T423E) was co-transfected with EGFP. Cells were visualized by fluorescence microscopy 20 hr after transfection. Cells were then photographed using a 100× objective lens. Where more than one cell is shown, the transfected cells, as observed by fluorescence microscopy, are indicated by an arrow. Cells transfected with empty vector EGFP, PAK1 (T423E), or PAK4 are shown in panels a, b, and c, respectively. Representative fields of PAK5, PAK5 (S573N), and PAK4 (S445N) expressing cells that exhibited filopodia but not neurites are shown in panels d, e, and f, respectively. Representative fields of cells exhibiting differentiated and extended neurites are shown in panels g, h, and i, respectively.

Figures 6A, 6B:
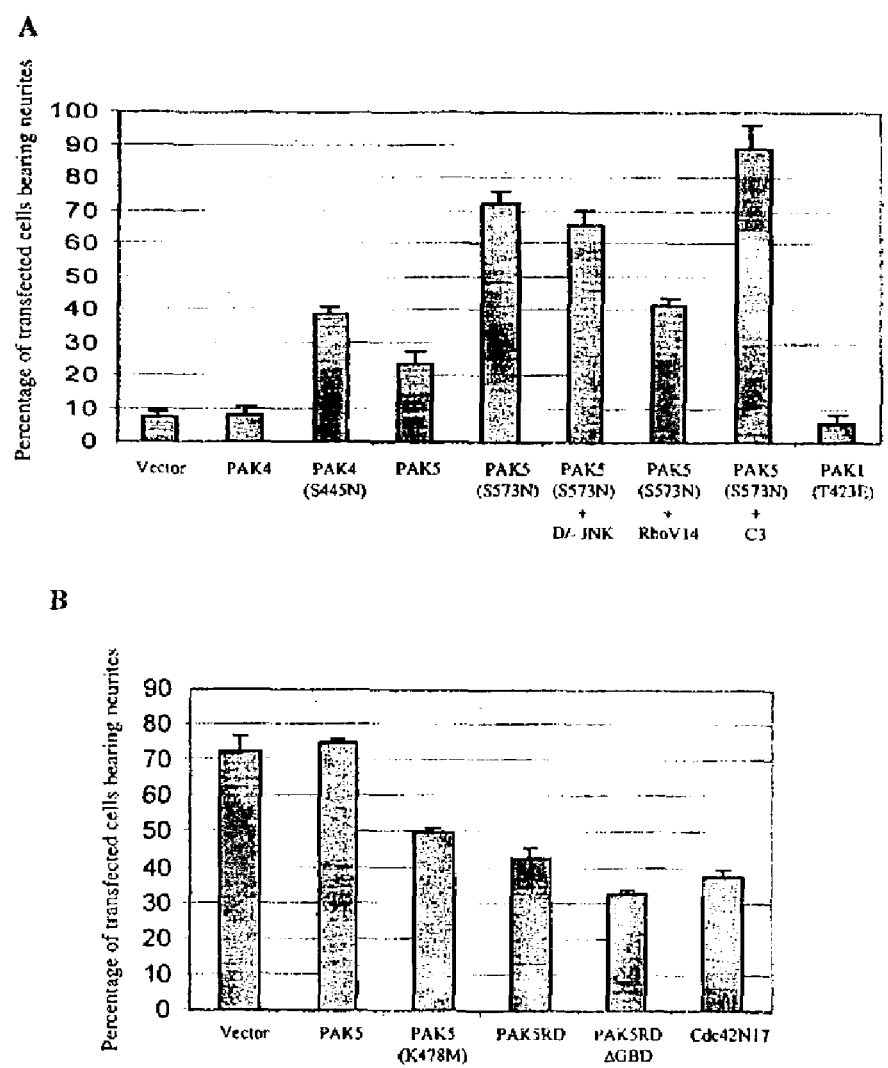

FIGS. 6A and 6B

Quantification of the effects of PAK5 on neurite formation. In Panel A, cells were transfected with EGFP expression vectors encoding the indicated proteins along with a threefold excess of either dominant-negative JNK, RhoV14, or C3 transferase as indicated. Following transfection, cells were grown in the presence of serum. Cells bearing neurites were counted and the percentage of transfected cells that had neurites is indicated. Co-transfection of PAK5 (S573N) vector with EGFP vector gave similar results as EGFP-PAK5 (S573N) (data not shown). In Panel B, Following transfection with the indicated expression vectors, cells were cultured in serum free medium for 72 hrs and cells bearing neurites were counted as in Panel A. Approximately 100 transfected cells were counted in each experiment. The results are an average of at least 2 independent experiments for each condition.

FIG. 7

Activated PAK5 inhibits Rho activity. 293 cells were transfected with wild-type Myc-RhoA expression vector together with equal amounts of either empty vector, wild-type EGFP-PAK5, or EGFP-PAK5 (S573N) expression vectors (without Myc tags). After transient expression, cell lysates were incubated with GST-Rhotekin glutathione agarose complexes, which bind specifically to GTP-loaded RhoA. Complexes were then washed and separated by SDS-PAGE, and the GTP RhoA content was analyzed by Western immunoblotting using and anti-Myc antibody. Total RhoA content is shown in the bottom panel.

DETAILED DESCRIPTION OF THE INVENTION

Definitions

As used in this application, except as otherwise expressly provided herein, each of the following terms shall have the meaning set forth below.

"Administering" shall mean delivery which is effected or performed using any of the various methods and delivery systems known to those skilled in the art. Administering can be performed, for example, intravenously, pericardially, orally, via implant, transmucosally, transdermally, intramuscularly, subcutaneously, intraperitoneally, intra-thecally, intralymphatically, intralesionally, or epidurally. Administering can be performed, for example, once, a plurality of times, and/or over one or more extended periods.

"Cytoskeletal reorganization" shall mean a change in the cytoplasmic filaments or microfilaments of a cell. Cytoskeletal reorganization includes, without limitation, an increase in the filamentous F- to monomeric G-actin ratio, the formation of condensed actin layers and intracellular actin polymerization.

"Immune cell" shall mean a cell involved specifically in an immune response, including but not limited to B-cells, T-cells, lymphocytes, antigen presenting cells and macrophages.

"Inhibit translation" shall mean to reduce the amount or rate of translation, or to stop translation entirely.

"Inhibit expression" shall mean to reduce the amount or rate of expression, or to stop expression entirely.

"Mammalian cell" shall mean any mammalian cell. Mammalian cells include, without limitation, cells which are normal, abnormal and transformed, and are exemplified by neurons, epithelial cells, muscle cells, blood cells, immune cells, stem cells, osteocytes, endothelial cells and blast cells.

"Migration" of a cell shall mean the movement or the extension of the cell from one point to another.

"Neurite outgrowth" shall mean an outgrowth from a neuron, as exemplified by axons and dendrites.

"Outgrowth" shall mean, with respect to a cell, a process which extends from the body of the cell. Outgrowths include, but are not limited to, long spindle processes, short spindle processes, long thick processes, short thick processes, long thin processes and short thin processes.

"PAK5 kinase substrate" shall mean a substrate which can be phosphorylated by PAK5. PAK5 kinase substrates include, but are not limited to, PAK5 and histone H4.

"PAK5 kinase activity" shall mean PAK5 phosphorylation of a PAK5 kinase substrate.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

"Protrusion formation" shall mean, with respect to a cell, any outward growth from the cell surface. Protrusion formations include, but are not limited to, filipodia, lamelopodia, outgrowths and spikes.

"Ruffle formation" shall mean, with respect to a cell, the formation of projections at the leading edge of the cell. Ruffle formation is observed especially in crawling cells, which appear to be ruffled.

"Spike" shall mean, with respect to a cell, a projection from the leading edge of the cell. Spikes include, for example, nerve growth cones and "microspikes", which are spikes measuring about 100 nm by 5-10 μm and supported by loosely bundled microfilaments.

"Subject" shall mean any mammal including, without limitation, a mouse, a rat, a dog, a guinea pig, a rabbit and a primate. In the preferred embodiment, the subject is a human being.

Embodiments of the Invention

This invention provides ten nucleic acids. The first nucleic acid is an isolated nucleic acid comprising a sequence encoding a mammalian PAK5 domain, with the proviso that the nucleic acid does not encode full-length human PAK5. In an embodiment of the first nucleic acid, the PAK5 domain is selected from the group consisting of a mammalian PAK5 GTPase-binding domain, a mammalian PAK5 regulatory domain and a mammalian PAK5 kinase domain.

The second nucleic acid comprises a sequence encoding a mammalian PAK5 GTPase-binding domain, but not a mammalian PAK5 kinase domain or a mammalian PAK5 regulatory domain.

The third nucleic acid comprises a sequence encoding a mammalian PAK5 kinase domain, but not a mammalian PAK5 GTPase-binding domain or a mammalian PAK5 regulatory domain.

The fourth nucleic acid comprises a sequence encoding a mammalian PAK5 regulatory domain, but not a mammalian PAK5 GTPase-binding domain or a mammalian PAK5 kinase domain.

The fifth nucleic acid comprises a sequence encoding a mammalian PAK5 GTPase-binding domain and a mammalian PAK5 regulatory domain, but not a mammalian PAK5 kinase domain.

The sixth nucleic acid comprises a sequence encoding a mammalian PAK5 GTPase-binding domain and a mammalian PAK5 kinase domain, but not a mammalian PAK5 regulatory domain.

The seventh nucleic acid comprises a sequence encoding a mammalian PAK5 regulatory domain and a mammalian PAK5 kinase domain, but not a mammalian PAK5 GTPase-binding domain.

In an embodiment of the first, fifth, sixth and seventh nucleic acids, the mammalian PAK5 is a human PAK5. In another embodiment of the first, fifth, sixth and seventh nucleic acids, the mammalian PAK5 is a murine PAK5. In an embodiment of the first nucleic acid, the nucleic acid comprises a sequence encoding murine PAK5.

The eighth nucleic acid is an isolated nucleic acid which specifically hybridizes to nucleic acid encoding a mammalian PAK5. In an embodiment of the eighth nucleic acid, the nucleic acid is DNA. In another embodiment of the eighth nucleic acid, the nucleic acid is RNA.

The ninth nucleic acid comprises a mammalian PAK5-encoding sequence operatively linked to an exogenous regulatory element. The tenth nucleic acid comprises a mammalian PAK5-encoding sequence operatively linked to an endogenous regulatory element. In an embodiment of the ninth and tenth nucleic acids, the nucleic acid is DNA. In another embodiment of the ninth and tenth nucleic acids, the nucleic acid is RNA.

This invention further provides a vector which comprises (a) the first, fifth, sixth, seventh, ninth or tenth nucleic acid or (b) a nucleic acid encoding the eighth nucleic acid. In one embodiment, the vector is selected from the group consisting of a plasmid, a cosmid, a bacteriophage and a eukaryotic virus. In a further embodiment, the above-mentioned eukaryotic virus is an adenovirus or a retrovirus.

This invention also provides a cell comprising the ninth or tenth nucleic acid. In an embodiment of this cell, the cell is selected from the group consisting of a bacterial cell, a fungal cell and an animal cell. In a further embodiment, the above-mentioned animal cell is selected from the group consisting of a neuron, an epithelial cell, a muscle cell, a blood cell, an immune cell, a stem cell, an osteocyte and an endothelial cell.

This invention further provides each of the proteins encoded by the first through the seventh nucleic acids.

This invention further provides compositions, each composition comprising a pharmaceutically acceptable carrier and one of the instant nucleic acids or proteins.

This invention provides methods for affecting cells with the instant nucleic acids and proteins. For the sake of convenience, the following nucleic acids and proteins are referred to collectively as "inducing agents": (a) the first nucleic acid comprising a sequence encoding a mammalian PAK5 kinase domain, but not a mammalian PAK5 GTPase-binding domain or a mammalian PAK5 regulatory domain; (b) the sixth, ninth, and tenth nucleic acids; (c) the protein encoded by the nucleic acid of (a); and (d) the protein encoded by the sixth nucleic acid. Also for the sake of convenience, the following nucleic acids and proteins are referred to collectively as "inhibiting agents": (a) the first nucleic acid comprising (i) a sequence encoding a mammalian PAK5 GTPase-binding domain, but not a mammalian PAK5 kinase domain or a mammalian PAK5 regulatory domain, or (ii) a sequence encoding a mammalian PAK5 regulatory domain, but not a mammalian PAK5 GTAase-binding domain or a mammalian PAK5 kinase domain; (b) the fifth, seventh, and eighth nucleic acids; (c) the proteins encoded by the nucleic acids of (a); and (d) the proteins encoded by the fifth, seventh, and eighth nucleic acids. Compositions comprising such agents are referred to herein as "inducing" or "inhibiting compositions," as appropriate.

The first method provides a method of inducing protrusion formation by a mammalian cell which comprises contacting a cell with an inducing agent in an amount effective to cause protrusion formation by a cell. In an embodiment of this method, the protrusion is a spike, an outgrowth, filopodia or lamelipodia. In the preferred embodiment, the outgrowth is a neurite outgrowth.

The second method is a method of causing cytoskeletal reorganization in a mammalian cell which comprises contacting the cell with an inducing agent in an amount effective to cause cytoskeletal reorganization in the cell.

The third method is a method of inducing ruffle formation on a mammalian cell, which comprises contacting the cell with an inducing agent in an amount effective to induce ruffle formation on the cell.

The fourth method is a method of inducing migration of a mammalian cell, which comprises contacting the cell with an inducing agent in an amount effective to induce migration of the cell.

The fifth method is a method of inducing proliferation of a mammalian cell, which comprises contacting the cell with an inducing agent in an amount effective to induce proliferation of the cell.

The sixth method provides a method of inhibiting protrusion formation by a mammalian cell, which comprises contacting the cell with an inhibiting agent in an amount effective to inhibit protrusion formation by the cell. In an embodiment of this method, the protrusion is a spike, an outgrowth, filopodia or lamelipodia. In the preferred embodiment, the outgrowth is a neurite outgrowth.

The seventh method is a method of inhibiting cytoskeletal reorganization in a mammalian cell, which comprises contacting the cell with an inhibiting agent in an amount effective to inhibit cytoskeletal reorganization in the cell.

The eighth method is a method of inhibiting ruffle formation on a mammalian cell, which comprises contacting the cell with an inhibiting agent in an amount effective to inhibit ruffle formation on the cell.

The ninth method is a method of inhibiting migration of a mammalian cell which comprises contacting the cell with an inhibiting agent in an amount effective to inhibit migration of the cell.

The tenth method is a method of inhibiting proliferation of a mammalian cell which comprises contacting the cell with an inhibiting agent in an amount effective to inhibit proliferation of the cell.

This invention further provides a method of inhibiting the transcription of a mammalian PAK5-encoding DNA molecule which comprises hybridizing the eighth ("hybridizing")

nucleic acid to the DNA molecule under conditions which would otherwise permit DNA transcription so as to inhibit transcription of the DNA molecule.

This invention further provides a method of inhibiting the translation of a mammalian PAK5-encoding mRNA molecule which comprises hybridizing the eighth ("hybridizing") nucleic acid to the mRNA molecule under conditions which would otherwise permit mRNA translation so as to inhibit translation of the mRNA molecule.

This invention further provides methods of use for the instant compositions in a subject. The first method provides a method of increasing neuronal outgrowth in a subject comprising administering to the subject an inducing composition in an amount effective to increase neuronal outgrowth in the subject. In an embodiment of this method, the subject is selected from the group consisting of a mouse, a rat, a rabbit, a dog, a guinea pig and a primate. In the preferred embodiment, the subject is a human.

The second method provides a method of inhibiting neuronal outgrowth in a subject comprising administering to the subject an inhibiting composition in an amount effective to increase the subject's neuronal outgrowth. In an embodiment of this method, the subject is selected from the group consisting of a mouse, a rat, a rabbit, a dog, a guinea pig and a primate. In the preferred embodiment, the subject is a human.

This invention further provides a method of determining whether a mammalian cell's reduced ability to form protrusions is due to blockage of signal transduction either upstream or at the level of PAK5, which comprises: (a) introducing PAK5 into the cell; and (b) determining whether its number of protrusions increases, such increase indicating that the cell's reduced ability to form protrusions is due to blockage of signal transduction either upstream or at the level of PAK5. In an embodiment of this method, the cell is a mouse cell, a rat cell, a rabbit cell, a dog cell, a guinea pig cell or a primate cell. In the preferred embodiment, the cell a human cell. Also in the preferred embodiment, the cell is selected from the group consisting of a neuron, an epithelial cell, a muscle cell, a blood cell, an immune cell, a stem cell, an osteocyte and an endothelial cell.

Finally, this invention provides a non-human transgenic mammal whose somatic cells lack PAK5-encoding DNA. In the preferred embodiment, the mammal is a mouse.

This invention will be better understood from the Experimental Details that follow. However, one skilled in the art will readily appreciate that the specific methods and results discussed are merely illustrative of the invention as described more fully in the claims which follow thereafter.

Experimental Details

This invention provides novel nucleic acids encoding a p21 activated kinase, PAK5, and related proteins which can induce or inhibit several cell functions including but not limited to: cellular outgrowth, cellular migration, cellular proliferation, cellular protrusion formation and cytoskeletal reorganization. PAK5 shares approximately 85% sequence identity with PAK4 in its kinase domain and GBD motif, but it is completely different from PAK4 throughout the rest of its regulatory domain. Like PAK4, PAK5 falls into the second category of PAKs based on its predicted amino acid sequence. Unlike PAK4, however, which is expressed in most tissues, PAK5 is expressed in only a limited number of tissues and it is especially highly expressed in the brain. This is of particular interest because PAK5 is similar to *Drosophila* MBT (28). MBT is thought to have a role in development, proliferation, or survival of cells in the mushroom body, a structure of *Drosophila* brain. Strikingly, expression of PAK5 triggered both filopodia formation and neurite outgrowth in N1E-115 cells. Constitutively active PAK5 had an even more dramatic effect than wild type PAK5, while dominant negative PAK5 mutants inhibited neurite outgrowth. In contrast to PAK5, activated PAK1 had no effect on neurite outgrowth in these cells. The results herein suggest that PAK5 is an important mediator in the signaling pathway by which Rho GTPases control the cytoskeletal changes that are necessary for promoting neurite outgrowth.

Materials and Methods

Cloning of PAK5

The EST database was screened using a Blast search in order to identify new members of the PAK family. EST clone ts97b05.x1 showed similarity to the kinase domain of mammalian PAK4 from amino acid 483 to the stop codon. To obtain the 5' end of the corresponding clone, a RT-PCR reaction was carried out using cDNA derived from human testis total RNA as a template. The 5' primer was a degenerate oligonucleotide corresponding to the sequence APSNFEH (SEQ ID NO:5) within the GBD domain of PAK4 and the 3' primer, agtagggagtgccaaccaat (SEQ ID NO:6) was an oligonucleotide corresponding to a region in ts97b05.x1 that differs from PAK4. The resulting PCR product was cloned and sequenced. Further screening of the database revealed that both the PCR product and ts97b05.x1 were homologous to human mRNA for KIAA1264. To obtain the full-length cDNA in one piece, another PCR reaction was carried out using oligonucleotides corresponding to the 5' and 3' ends of KIAA1264. The full-length PCR product was designated PAK5. Later PAK5 was also found to be nearly identical to GenBank clone ABO40812.

Plasmids cDNA encoding PAK5, PAK5RD, and PAK5RDΔGBD were subcloned between the ClaI and EcoRI sites on pCAN-Myc1 expression vector containing a Myc epitope tag. PAK5RD, corresponding to amino acid 1 to 451, is the amino-terminal part of PAK5 without the kinase domain, and was generated by PCR using PAK5 cDNA as the template. PAK5RDΔGBD, corresponding to amino acids 31 to 451, lacks both the kinase domain and the GBD domain, and was generated by PCR using PAK5 cDNA as the template. Constitutively active PAK5 (S573N) in pCAN-Myc1 was generated by site-directed mutagenesis (Stratagene QuickChange kit) and contains a serine to glutamic acid substitution at amino acid 602 which is a putative autophosphorylation site, and a serine to asparagine substitution at amino acid 573 within the kinase domain. PAK5 (K478M) was also generated by site-directed mutagenesis and contains a lysine to methionine substitution at amino acid 478. cDNAs encoding PAK5, PAK5 (S573N), and PAK5 (K478M) were also subcloned between the HindIII and SacII sites on pEGFP-C3 (Clontech) expression vector to obtain PAK5-EGFP vectors. Myc-tagged PAK4 is described in (1). HA-tagged JNK, GST-c-Jun and MEKK1Δ are described in (31). Dominant negative JNK has point mutations in which its two phosphorylation sites (Thr-183 and Tyr-185) are converted to Ala and Phe, respectively, and is described in (9). Cdc42V12, Rac V12, and RhoV14 are described (30).

Northern Blots

Northern analysis was performed using a human multiple tissue RNA blot (Clontech). Hybridization and washes were carried out as recommended by the manufacturer. The probe was a 400 bp fragment from within the PAK5 kinase domain that differs in sequence from PAK4 or any other sequences in the GenBank database. The probe was labeled with [α-$^{32}$P] dCTP (Amersham) by using a random priming kit (Stratagene).

Overlay Assay

The overlay assay is described in (27). Briefly, 293 cells were transfected with 10 µg of empty vector, MycPAK4, or Myc-PAK5. PAK4 and PAK5 were then immunopurified using anti-Myc antibody (9E10, Santa Cruz) and the immunopurified proteins were separated on SDS-PAGE and transferred to a PVDF membrane. The membrane was then washed and blocked with phosphate-buffered saline (PBS) containing 1% bovine serum albumin (BSA) and 100 mM dithiothreitol (DTT). Recombinant GTPases (2 µg) were pre-loaded with [γ-$^{32}$P] GTP and were incubated for 5 min with the PVDF membrane. The membrane was washed for 5 min and was exposed to a film for 2 hr.

Production of GST-C21 Fusion Protein and Rho GTPase Activity Assays

GST-C21 contains the N-terminal 90 amino acids of the Rho effector protein Rhotekin, consisting of the Rho binding domain. *Escherichia coli* BL21 transformed with the GST-C21 construct was grown at 30° C. to an optical density at 600 nm of 0.30. Expression and purification of the fusion protein and the GTPase activity assays were performed as described in Sander et al. (1999). In brief, lysates were prepared from 293 cells that were transfected with Myc-RhoA expression vector together with either empty vector, PAK5, or activated PAK5 vector. Lysates were then incubated with bacterially expressed GST-C21 fusion proteins bound to glutathione-coupled agarose beads. The beads and the bound proteins were washed three times with an excess of lysis buffer and then eluted with Laemmli sample buffer. The bound RhoA proteins were analyzed by Western blotting with antibody against the Myc tag. A portion of the lysate was saved for direct Western blot analysis with ant-Myc antibody.

Preparation of Recombinant Proteins

Recombinant GST-c-Jun, GST-Rac1V12 and GST-Cdc42V12 were prepared as described (42).

Cell Culture and Transfection

All cells were grown at 37° C. in 5% $Co_2$. 293 and N1E-115 cells were cultured in Dulbecco's Modified Eagle's medium (DMEM) containing 10% fetal bovine serum (GibcoBRL). For transfections in 293 cells, a total of 10 µg of DNA was transfected into the cells in 10 cm plates (60% confluent) using the calcium phosphate precipitation method. For N1E-115 cells, 4 µg of total DNA was transfected into the cells, using FuGENE6 (Roche), in 35 mm wells (seeded 1×10$^4$ cells per well) containing coverslips that were precoated with 10 µg ml$^{-1}$ mouse laminin (GibcoBRL) for 1 hr at 37° C.

Western Blots

Western blots were carried out as described (1).

Protein Kinase Assays

To assay histone H4 (HH4) phosphorylation by the PAKs, 293 cells were transfected with 10 µg of empty vector, Myc-PAK4, or Myc-PAK5 (wild type or constitutively active) expression vectors. Cells were harvested in M2 buffer (32) 48 hr after transfection. Equal amounts of the Myc-tagged proteins, as assayed with Western blot, were then immunopurified from approximately 100 µg of cell extracts using antibody generated against the Myc epitope tag (9E10, Santa Cruz) and protein A sepharose. After 2 hr incubation at 4° C., the immunoprecipitates were washed twice in M2 buffer and twice in a buffer containing 20 mM HEPES (pH 7.5) and 10 mM $MgCl_2$, then incubated together with 5 µg HH4, in a buffer containing 20 mM HEPES (pH 7.5), 10 mM $MgCl_2$, 20 mM β-glycerol phosphate, 10 mM PNPP, 1 mM DTT, 50 µM $Na_3VO_4$, 20 µM ATP, and 5 µCi [γ-$^{32}$P] ATP for 20 min at 30° C. The reaction was terminated with SDS-PAGE sample buffer, followed by SDS-PAGE and autoradiography.

To analyze the kinase activity of hemagglutinin (HA)-tagged JNK, 293 cells were transfected with either 10 µg of empty vector or 5 µg of HA-tagged JNK expression vector in the absence or presence of increasing doses of Myc-PAK5 (1, 3, and 5 µg), or expression vectors containing Rac2L61 (2.5 µg), or MEKK1Δ (2.5 µg). The total amount of DNA in each transfection was kept at 10 µg using empty vector. Cells were harvested 48 hr after transfection and the amount of HA-JNK in cell lysates was normalized by Western blot. Equal amounts of HA-JNK were then immunopurified from approximately 100 µg of cell lysates using an anti-HA antibody (12CA5, Boehringer Mannheim) and protein A sepharose in M2 buffer at 4° C. for 2 hr. The protein A sepharose beads were then washed twice in M2 buffer, and twice in a buffer containing 20 mM HEPES (pH 7.5) and 10 mM $MgCl_2$, then incubated in a buffer containing 20 mM HEPES (pH 7.5), 10 mM $MgCl_2$, 20 mM β-glycerol phosphate, 10 mM PNPP, 1 mM DTT, 50 µM $Na_3VO_4$, 20 µM ATP, and 5 µCi [γ-$^{32}$P] ATP, together with 2 µg purified recombinant GST-c-Jun for 20 min at 30° C. The reaction was terminated with SDS-PAGE sample buffer, followed by SDS-PAGE and autoradiography. The phosphorylation of cJun was quantitated by phosphorimager analysis.

Immunofluorescence

After transient transfection, N1E-115 cells were fixed in 3% paraformaldehyde for 20 min, permeabilized in 0.1% Triton X-100, and blocked with 5% goat serum for 20 min at room temperature. Cells were stained for the presence of Myc-PAK5, Myc-PAK5 (K478M), Myc-PAK5RD, Myc-PAK5RDΔGBD, or Myc-Cdc42N17 with mouse anti-Myc antibody (9E10, Santa Cruz), then incubated with goat anti-mouse IgG conjugated with rhodamine (PIERCE).

Neurite Outgrowth Scoring Assay

N1E-115 cells were grown on coverslips precoated with mouse laminin, in 35 mm wells, and transfected with 4 µg of the indicated expression vectors. 20 hr after transfection, N1E-115 were examined by fluorescence microscopy to detect the presence of the green fluorescent cells that contain the transfected plasmids. Transfected cells bearing neurite-like structure with a length of at least one cell body were counted and scored as the percentage of total transfected cells. The images were taken either with a Nikon DIAPHOT 300 inverted microscope with epi-fluorescence attachments and a color CCD camera using a 10× objective lens, or with a Nikon OPTIPHOT-2 fluorescence microscope and a digital camera using a 60× objective lens.

Generation of PAK5 and PAK4 Knockout Mice

A PAK5 targeting vector was generated by replacing exon 3, which contains the critical part of the kinase domain, with a neomycin resistance gene. This vector was electroporated into ES cells, and G418 resistant clones were isolated. Southern blot analysis revealed that three clones contained the desired homologous recombination event. These clones were injected into blastocysts to generate chimeras. The chimeras were then crossed to generate PAK5 heterozygotes. PAK5 heterozygous mice were crossed to give rise to PAK5 null mice.

An alternative targeting vector has also been generated in which exon 1 is deleted instead of exon 3. Exon 1 contains the start codon and the GTPase Binding domain. Using procedures similar to the ones described above, chimeras were generated using this vector. These chimeras will be backcrossed to generate PAK5 heterozygotes and PAK5 knockouts as described above.

Results

Identification of PAK5, a Novel Member of the PAK Family of Kinases

Figure 1C:
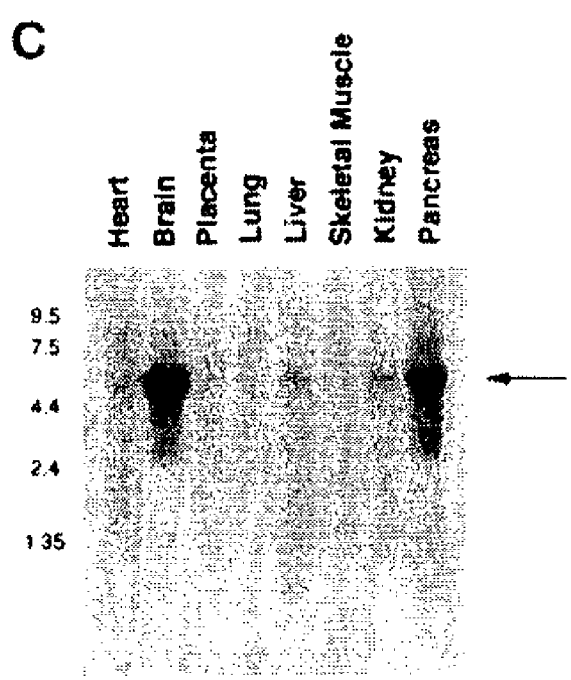
FIG. 1A

The human PAK5 cDNA was cloned as described in the Materials and Methods section. The sequence of the full-length PAK5 and the predicted amino acid sequence are shown in FIG. 1A. The kinase domain, comprising amino acids 10-30, and the GBD domain, comprising amino acids 452-702, are underlined in the figure. A comparison between the amino acid sequences of these domains and those of hPAK4, MBT, hPAK6 and hPAK1 demonstrated that PAK5 shares surprising homology to the *Drosophila* MBT protein. MBT is expressed in the mushroom body, a structure of the *Drosophila* brain. For example, the PAK5 kinase domain shares an 80% sequence identity with the same domain of MBT (from amino acids 371-620 of MBT). This is only slightly less than its 84% sequence identity PAK5 shares with the same domain of PAK4 (from amino acids 324-573 of PAK4), and significantly greater than its 76% and 57% identity with the kinase domains of PAK6 and PAK1, respectively (from amino acids 273-523 of PAK1; and from amino acids 420-659 of PAK6). PAK5 shares similarly high sequence homology with MBT in the GBD domain. The GBD domain shares 86%, 76%, 70%, and 57% identity with the corresponding domains of PAK4 (from amino acids 10-30 of PAK4), MBT (from amino acids 10-30 of MBT), PAK6 (from amino acids 10-30 of PAK6) and PAK1 (from amino acids 74-94 of PAK1), respectively. Outside of the GBD and kinase domains, there is little sequence homology between PAK5 and either PAK4 or any other known proteins. Furthermore, no obvious SH3 domain recognition sites or Gβγ binding domains similar to those in PAK1 are evident in PAK5. Northern analysis of PAK5 indicates that it is expressed in brain and pancreas. Very little or no PAK5 could be detected in several other human tissues that were examined (data not shown).

PAK5 Interacts with GTP-bound Rac and Cdc42Hs

Figure 2:
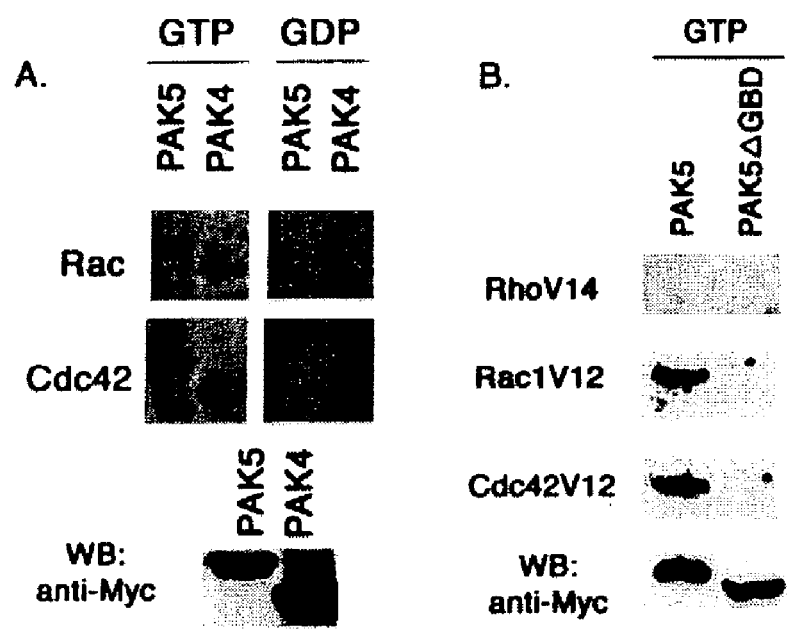

Sequencing analysis indicates that PAK5 has a putative GBD/CRIB motif similar to that of PAK4. PAK4 binds strongly to Cdc42 and more weakly to Rac through this domain. To determine whether PAK5 interacts with the GTPases, an overlay assay was used in which filters containing immobilized PAK4 and PAK5 were probed with GTP loaded Rac1V12 or Cdc42V12. We found that PAK5 interacts with both Cdc42 and Rac (FIG. 2), suggesting that PAK5 is a target for these GTPases. Like PAK4, however, PAK5 appeared to interact more tightly with Cdc42 than Rac. PAK5 did not bind to GTP-loaded RhoA, and a PAK5 mutant lacking the GBD (PAK5ΔGBD) was not able to bind to Cdc42 or Rac.

PAK5 Autophosphorylates and Phosphorylates an Exogenous Substrate

Previously, it was shown that wild type PAK4 can autophosphorylate and phosphorylate Histone H4 (HH4) (1), and that a constitutively active PAK4, PAK4 (S445N), has stronger kinase activity than wild type PAK4 (36). PAK4 (S445N) has a serine to glutamic acid mutation at the putative autophosphorylation site (amino acid 474) and a serine to asparagine mutation at amino acid 445, which is thought to function by stabilizing the catalytic loop (36, 48). This mutant has an elevated level of kinase activity, but its substrate specificity does not appear to be altered and it does not induce nonspecific morphological changes (36).

In order to determine whether PAK5 functions similarly, 293 cells were transfected with Myc-tagged PAK5 expression vector or Myc-tagged PAK5 (S573N), which contains the analogous mutations to PAK4 (S445N). Myc-tagged wild type PAK4 expression vector was used for comparison. Equal amounts of PAK5, PAK5 (S573N), and PAK4 (as assessed by Western blots) were immunopurified from cell lysates and incubated with Histone H4 (HH4) in kinase buffer with $[\gamma-{}^{32}P]$ ATP. Autophosphorylation and HH4 phosphorylation were analyzed after SDS-PAGE and autoradiography (FIGS. 3A and 3B). The results indicate that both PAK5 and PAK5 (S573N) could autophosphorylate and phosphorylate HH4, although the kinase activity of PAK5 (S573N) was stronger than that of wild type PAK5 (FIG. 3A). Wild type PAK5 had significantly stronger activity than an equivalent amount of PAK4. In fact, the autoradiogram had to be overexposed relative to PAK5 activity, in order to detect PAK4 activity (FIG. 3B).

PAK5 Activates the JNK Pathway

Figure 4:
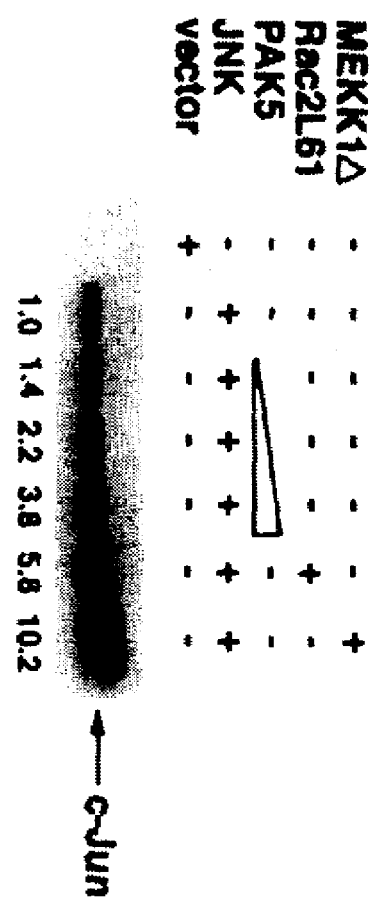

In addition to regulation of the actin cytoskeleton, one of the functions of Cdc42Hs and Rac is to activate the JNK MAP Kinase pathway (2, 4, 6, 30, 52). Since PAK5 interacts with Rac and Cdc42, its ability to activate JNK was tested. 293 cells were transfected with a HA-tagged JNK expression vector together with increasing doses of an expression vector containing the PAK5 cDNA. Activated Rac and MEKK1 expression vectors were used as positive controls. After transient expression, JNK was immunopurified from cell lysates, followed by an in vitro kinase assay using GST-c-Jun as a substrate. The results indicate that overexpression of the wild type PAK5 led to activation of the JNK pathway that was almost as strong as activation by Rac (FIG. 4). In contrast, PAK4 activation of JNK was significantly lower than Rac activation (1). PAK5 did not activate the ERK pathway and it only inefficiently activated the p38 pathway (data not shown).

Figure 5:
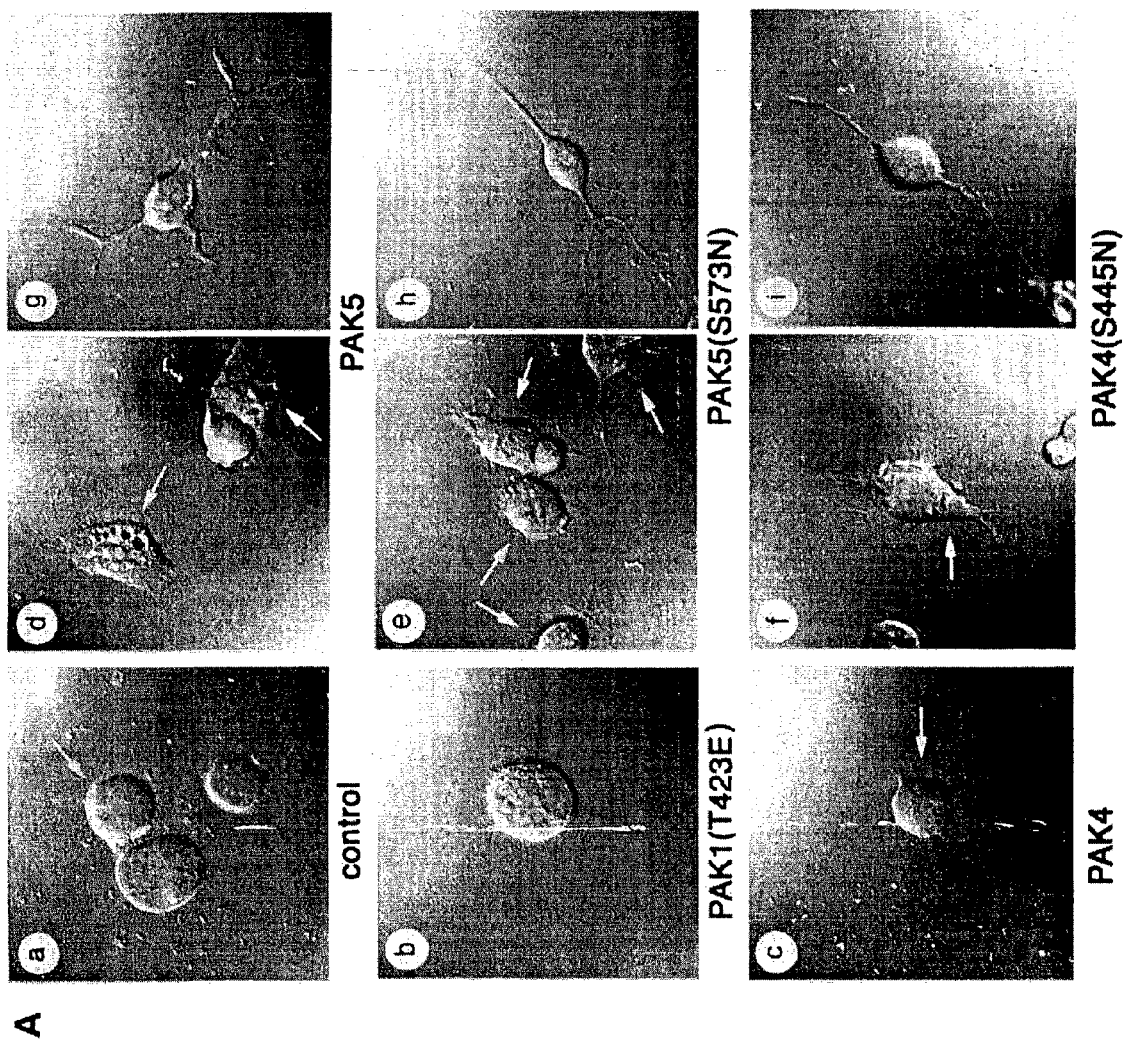

Expression of PAK5 Leads to the Formation of Filopodia and Neurite Processes in N1E-115 Cells To determine whether expression of PAK5 could promote morphological changes in neuronal cells, N1E-115 neuroblastoma cells grown in the presence of serum were transiently transfected with either empty vector containing only Enhanced GFP (EGFP) or expression vectors containing PAK5 or PAK5 (S573N) fused to EGFP. For comparison, cells were transfected with a vector containing activated PAK1 (T423E). Cells transfected with EGFP alone appeared similar to non-transfected cells. Most of the cells had rounded morphologies, and approximately 7% of them had neurite-like extensions. In contrast, at least three times as many PAK5-expressing cells had neurite-like processes. Most strikingly, expression of PAK5 (S573N) led to the production of long neurite-like processes in approximately 70% of the transfected cells. In both PAK5- and PAK5 (S573N)-expressing cells, even the cells that did not have neurites had a dramatic increase in filopodia. In contrast to PAK5, expression of PAK1 (T423E) did not lead to the increased production of either filopodia or neurites in these cells. Representative cells from each condition visualized at 60× magnification are shown in FIG. 5A. FIG. 5B shows fields of cells expressing empty vector, PAK1 (T423E), or PAK5 (S573N) visualized at a 10× magnification. The percentages of neurite bearing cells under the different conditions are summarized in FIG. 6A.

Figure 7:
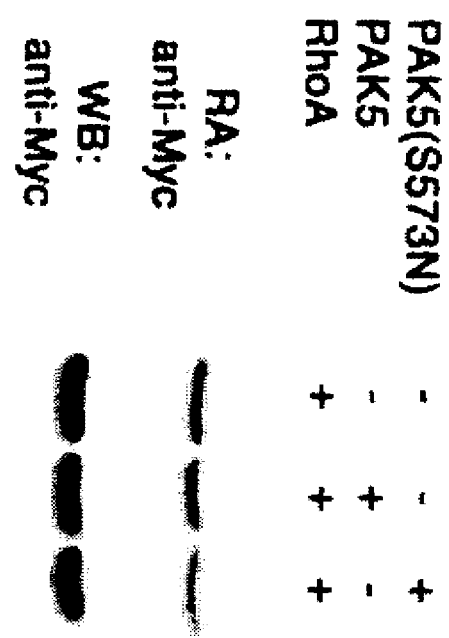

The Cdc42 and Rac pathways appear to function antagonistically with the Rho pathway in N1E-115 cells, where Cdc42 and Rac are required for neurite outgrowth and Rho causes neurite retraction (19, 40, 51). To see whether PAK5 functions antagonistically with Rho, cells were transfected with PAK5 (S573N) together with an activated RhoAV14 vector. Expression of RhoAV14 caused a significant reduction in the percentage of PAK5 (S573N) transfected cells bearing neurites (see FIG. 6A). In contrast, approximately 90% of cells transfected with PAK5 and the Rho inhibitor C3 transferase had neurites. Dominant-negative JNK had no inhibitory effect on neurite outgrowth (see FIG. 6A), although it effectively blocked MEKK activation of the c-Jun promoter (data not shown). The results indicate that PAK5 triggers neurite outgrowth by a pathway that functions antagonistically to the Rho pathway and that is independent of JNK activation. To test whether PAK5 can actually inhibit RhoA activity, 293 cells were transfected with wild-type RhoA together with either empty vector, wild-type PAK5 or PAK5 (S573N), and RhoA activity was assessed by a Rhotekin binding assay. As shown in FIG. 7, activated PAK5 caused a significant reduction in the amount of activated Rho, but had no effect on total RhoA levels.

PAK5 is Necessary for Neurite Outgrowth in N1E-115 Cells

To see whether PAK5 is necessary for neurite outgrowth, N1E-115 cells were transfected with either empty vector or vectors containing one of three different dominant negative PAK5 mutants; PAK5 (K478M) has a single point mutation within the kinase domain rendering it kinase inactive, PAK5RD lacks the kinase domain, and PAK4RDΔGBD lacks the kinase domain and the GBD domain. After transient transfection cells were changed to serum free media to induce neurite outgrowth and cells were observed 72 hours later. While approximately 70% of the empty vector transfected cells had neurites, expression of each of the dominant negative mutants led to a reduction in the percentage of neurite bearing cells. The levels of inhibition by the dominant negative PAK5 mutants were similar to the level of inhibition that resulted from expression of dominant negative Cdc42N17. Expression of wild-type PAK5 did not cause any inhibition in neurite outgrowth. These results are summarized in FIG. 6B. Taken together, these results indicate that PAK5 is both necessary and sufficient to induce neurite outgrowth in N1E-115 cells.

PAK5 Heterozyous and Knockout Mice

Mice heterozygous for PAK5 deletion were generated as described in the Methods section and PAK5 null mice were generated by breeding the heterozygotes. Crosses between two PAK5 heterozygotes gave rise to wild-type (+/+), PAK5 heterozygous (+/−), and PAK5 knockout (−/−) offspring, as assessed by PCR analysis and Southern blot analysis of tail DNA. Western blot analysis of brain lysates will be carried out to confirm the absence of PAK5 protein in the (−/−) mice. PAK5 (−/−) mice are both viable and fertile.

Discussion

Described here is the characterization of a novel member of the mammalian PAK family, PAK5, which interacts specifically with GTP-loaded Cdc42 and more weakly with Rac. PAK5 shares sequence homology with PAK4 within the GBD and kinase domains, although there is very little sequence similarity between these two protein kinases outside of these domains. Unlike PAK4, PAK5 is only expressed in a limited number of tissues, and it is especially highly expressed in the brain. In this regard it is intriguing that PAK5 shares sequence similarity with *Drosophila* MBT (28), a kinase which is thought to regulate growth of cells in the mushroom body of *Drosophila* brain. PAK5 is therefore an excellent candidate for a Cdc42/Rac target that regulates growth and morphology in neuronal cells.

Cytoskeletal organization is a critical part of neuronal development. For example, filopodia and lamellipodia play key roles in the guidance of neuronal growth cones towards attractive cues and away from repulsive cues, and neurite extension occurs when these filopodia and lamellipodia are stabilized. Stabilization of these structures is followed by extension of new filopodia and lamellipodia so that the cycle of axon guidance and growth can continue (24, 33). Because the formation of filopodia and lamellipodia is so important for neurite outgrowth and growth cone guidance, there has been considerable interest in the possible role for the Rho GTPases in these processes. Of particular interest are Cdc42 and Rac, which were first described as proteins that regulate filopodia and lamellipodia formation in fibroblasts. Both Cdc42 and Rac have subsequently been found to play key roles in all aspects of neural development, including growth cone guidance and the extension of axons (24).

The effector proteins that mediate the morphological changes induced by the Rho GTPases in neuronal cells are not yet clearly defined. The PAK serine/threonine kinases are good candidates because they are direct targets of Cdc42 and Rac. PAKs 1, 2, and 3, however, may not be directly involved in all of the cytoskeletal changes induced by these GTPases, and effector mutants of Cdc42 and Rac that can not bind to them can still induce filopodia and lamellipodia (13, 21). In contrast, PAK4, which is the founding member of a new group of PAKs, directly regulates filopodia formation in response to Cdc42. PAK4 has a modified GTPase Binding Domain (GBD) compared with the previously identified PAKs, and it can even bind to Cdc42 effector mutants that do not bind PAKs 1, 2, and 3, via this domain (1). PAK5 is similar to PAK4 in sequence, especially with the GBD and kinase domains, but it is expressed primarily in the brain. PAK5 is therefore envisioned in this invention as a target for the GTPases involved in neurite outgrowth.

While members of the drosophila PAK family, including *Drosophila* PAK and MBT, are thought to be involved in neuronal development (12, 34), the roles for mammalian PAKs in neurogenesis are less well defined. It was found that expression of activated PAK5 led to a dramatic increase in the formation of neurite-like extensions in N1E-115 cells. Even in the subset of PAK5-expressing cells in which neurites were not seen, there was an increased production of filopodia, which is an important step in the production of neurite processes. The instant results suggest, therefore, that PAK5 in fact is a major target for Cdc42, and possibly Rac, in neuronal cells, which regulates the formation of filopodia and neurite processes. Previous work has shown that PAK1 can also trigger neurite outgrowth in PC12 cells. However, this required that it be targeted to the membrane by addition of a membrane targeting sequence, and it occurred by a mechanism that did not require its kinase activity or its Cdc42/Rac binding domain (GBD). PAK1 might therefore function as a type of scaffolding protein which recruits other proteins to the membrane where they can promote neurite outgrowth (8). It was found here that activated PAK1 did not promote neurite outgrowth in N1E-115 cells. In contrast, PAK5 clearly triggered both filopodia formation and neurite outgrowth in these cells. This did not require membrane targeting of PAK5, and the extent of neurite outgrowth was directly related to the level of its kinase activity. The instant results suggest, therefore, that PAK5 regulates the morphology of these cells by phosphorylating target proteins that are specifically involved in neurite outgrowth. The substrates for PAK5 and the mechanism by which it triggers neurite outgrowth in N1E-115 cells remain to be elucidated. One possibility is that like Cdc42 and Rac, PAK5 may promote neurite outgrowth by a mechanism that is antagonistic to Rho (19, 40, 51). Consistent with this, it was found that overexpression of a constitutively active Rho mutant, RhoV14, blocks neurite production by activated PAK5. It will be interesting to determine, therefore, whether PAK5 functions by inhibiting the activity of Rho. It was also found that, like Cdc42 and Rac (2, 4, 6, 30, 52), PAK5 activates the JNK pathway. However, while JNK has been implicated in PC12 cell differentiation (15, 16, 23), it was shown to be dispensable for differentiation of N1E-115 cells (40), and it was found that a kinase inactive JNK has no inhibitory effect on neurite outgrowth triggered by PAK5. These results therefore suggest that JNK is part of a parallel PAK5-activated pathway, and not part of the pathway leading to morphological changes.

The *Drosophila* protein MBT is quite similar to PAK5 in sequence, especially within the kinase domain and GBD motif. Interestingly, disruption of the mbt gene leads to a reduction in the number of cells in the mushroom body of *drosophila* brain. MBT was therefore proposed to be involved in the regulation of proliferation or survival of neuronal cells (28). It is interesting to note that cell death in the developing nervous system can result from improper connections, or lack of connections, between neurons and their targets (41). Since MBT is similar to PAK5 in sequence, an intriguing possibility is that cell death in mbt mutant flies might occur because cells fail to develop axons properly and therefore fail to make their proper connections. Another possibility is that MBT and PAK5 could specifically trigger cell survival pathways. In this regard it is interesting that PAK5 activated JNK, since the JNK pathway has been implicated in the regulation of cell growth in mammalian cells (29), and it is thought to contribute to both survival and apoptosis in different parts of the brain (20).

REFERENCES

1. Abo, A., J. Qu, M. S. Cammarano, C. Dan, A. Fritsch, V. Baud, B. Belisle, and A. Minden 1998. PAK4, a novel effector for Cdc42Hs, is implicated in the reorganization of the actin cytoskeleton and in the formation of filopodia *EMBO J*. 17:6527-6540.
2. Bagrodia, S., B. Derijard, R. J. Davis, and R. A. Cerione 1995. Cdc42 and PAK-mediated signaling leads to Jun kinase and p38 mitogen-activated protein kinase activation *J Biol Chem*. 270:27995-27998.
3. Berninger, B., and M. Poo 1996. Fast actions of neurotrophic factors. *Curr Opin Neurobiol*. 6:324-330.
4. Brown, J. L., L. Stowers, M. Baer, J. Trejo, S. Coughlin, and J. Chant 1996. Human Ste20 homologue hPAK1 links GTPases to the JNK MAP kinase pathway. *Curr Biol*. 6:598-605.
5. Brown, M. D., B. J. Cornejo, and J. R. Bamburg 2000. Cdc42 Stimulates Neurite Outgrowth and Formation of Growth Cone Filopodia and Lamellipodia. *J Neurobiol*. 43:352.
6. Coso, O. A., M. Chiariello, J. C. Yu, H. Teramoto, P. Crespo, N. Xu, T. Miki, and J. S. Gutkind 1995. The small GTP-binding proteins Rac1 and Cdc42 regulate the activity of the JNK/SAPK signaling pathway. *Cell* 81:1137-1146.
7. Daniels, R. H., and G. M. Bokoch 1999. p21-activated protein kinase: a crucial component of morphological signaling? *Trends Biochem Sci*. 24:350-355.
8. Daniels, R. H., P. S. Hall, and G. M. Bokoch 1998. Membrane targeting of p21-activated kinase 1 (PAK1) induces neurite outgrowth from PC12 cells. *EMBO J*. 17:754-764.
9. Derijard, B., M. Hibi, I. H. Wu, T. Barrett, B. Su, T. Deng, M. Karin, and R. J. Davis 1994. JNK1: a protein kinase stimulated by UV light and Ha-Ras that binds and phosphorylates the c-Jun activation domain. *Cell* 76:1025-1037.
10. Dutartre, H., J. Davoust, J. P. Gorvel, and P. Chavrier 1996. Cytokinesis arrest and redistribution of actin-cytoskeleton regulatory components in cells expressing the Rho GTPase CDC42Hs. *J Cell Sci*. 109:367-377.
11. Gebbink, M. F., O. Kranenburg, M. Poland, F. P. van Horck, B. Houssa, and W. H. Moolenaar 1997. Identification of a novel, putative Rho-specific GDP/GTP exchange factor and a RhoA-binding protein: Control of neuronal morphology. *J Cell Biol*. 137:1603-1613.
12. Hing, H., J. Xiao, N. Harden, L. Lim, and S. L. Zipursky 1999. Pak Functions Downstream of Dock to regulate photoreceptor axon guidance in Drosophilia. *Cell* 97:853-863.
13. Joneson, T., M. McDonough, D. Bar-Sagi, and L. Van Aelst 1996. RAC regulation of actin polymerization and proliferation by a pathway distinct from Jun kinase. *Science* 274:1374-1376.
14. Kaufmann, N., Z. P. Wills, and D. Van Vactor 1998. *Drosophila* Rac1 controls motor axon guidance. *Development* 125:453-61.
15. Kick, G., G. Messer, G. Plewig, P. Kind, and A. E. Goetz 1996. Strong and prolonged induction of c-jun and c-fos proto-oncogenes by photodynamic therapy. *Br J Cancer* 74:30-36.
16. Kita, Y., K. D. Kimura, M. Kobayashi, S. Ihara, K. Kaibuchi, S. Kuroda, M. Ui, H. Iba, H. Konishi, U. Kikkawa, S. Nagata, and Y. Fukui 1998. Microinjection of activated phosphatidylinositol-3-kinase induces process outgrowth in rat PC12 cells through the Rac-JNK signal transduction pathway. *J Cell Sci*. 111:907-915.
17. Knaus, U. G., and G. M. Bokoch 1998. The p21Rac/Cdc42-activated kinases (PAKs) *Int J Biochem Cell Biol*. 30:857-862.
18. Kozma, R., S. Ahmed, A. Best, and L. Lim 1995. The Ras-related protein Cdc42Hs and bradykinin promote formation of peripheral actin microspikes and filopodia in Swiss 3T3 fibroblasts. *Mol Cell Biol*. 15:1942-1952.
19. Kozma, R., S. Sarner, S. Ahmed, and L. Lim 1997. Rho family GTPases and neuronal growth cone remodelling: relationship between increased complexity induced by Cdc42Hs, Rac1, and acetylcholine and collapse induced by RhoA and lysophosphatidic acid. *Mol Cell Biol*. 17:1201-1211.
20. Kuan, C. -Y., D. Yang, D. R. Samanta Roy, R. J. Davis, P. Rakic, and R. A. Flavell 1999. The Jnk1 and Jnk2 protein kinases are required for regional specific apoptosis during early brain development. *Neuron* 22:667-676.
21. Lamarche, N., N. Tapon, L. Stowers, P. D. Burbelo, P. Aspenstrom, T. Bridges, J. Chant, and A. Hall 1996. Rac and Cdc42 induce actin polymerization and G1 cell cycle progression independently of p65PAK and the JNK/SAPK MAP kinase cascade. *Cell* 87:519-529.
22. Lamoureux, P., Z. F. Altun-Gultekin, C. Lin, J. A. Wagner, and S. R. Heidemann 1997. Rac is required for growth cone function but not neurite assembly. *J Cell Sci*. 110:635-641.

23. Leppa, S., R. Saffrich, W. Ansorge, and D. Bohmann 1998. Differential regulation of c-Jun by ERK and JNK during PC12 cell differentiation. *EMBO J.* 17:4404-4413.

24. Luo, L. 2000. Rho GTPases in neuronal morphogenesis. *Nat Rev Neurosci.* 1:173-180.

25. Luo, L., Y. J. Liao, L. Y. Jan, and Y. N. Jan 1994. Distinct morphogenetic functions of similar small GTPases: *Drosophila* Drac1 is involved in axonal outgrowth and myoblast fusion. *Genes Dev.* 8:1787-802.

26. Manser, E., H. Y. Huang, T. H. Loo, X. Q. Chen, J. M. Dong, T. Leung, and L. Lim 1997. Expression of constitutively active alpha-PAK reveals effects of the kinase on actin and focal complexes. *Mol Cell Biol.* 17:1129-1143.

27. Martin, G. A., G. Bollag, F. McCormick, and A. Abo 1995. A novel serine kinase activated by rac1/CDC42Hs-dependent autophosphorylation is related to PAK65 and STE20. *EMBO J.* 14:1970-1978.

28. Melzig, J., K. H. Rein, U. Schafer, H. Pfister, H. Jackie, M. Heisenberg, and T. Raabe 1998. A protein related to p21-activated kinase (PAK) that is involved in neurogenesis in the *Drosophila* adult central nervous system. *Curr Biol.* 8:1223-1226.

29. Minden, A., and M. Karin 1997. The JNK family of MAP Kinases: regulation and function, p. 209-233. In B. W. O'Malley (ed.), Hormones and Signaling, vol. 1. Academic Press, San Diego.

30. Minden, A., A. Lin, F. X. Claret, A. Abo, and M. Karin 1995. Selective activation of the JNK signaling cascade and c-Jun transcriptional activity by the small GTPases Rac and Cdc42Hs. *Cell* 81:1147-1157.

31. Minden, A., A. Lin, M. McMahon, C. Lange-Carter, B. Derijard, R. J. Davis, G. L. Johnson, and M. Karin 1994. Differential activation of ERK and JNK mitogen-activated protein kinases by Raf-1 and MEKK. *Science* 266:1719-1723.

32. Minden, A., A. Lin, T. Smeal, B. Derijard, M. Cobb, R. Davis, and M. Karin 1994. c-Jun N-terminal phosphorylation correlates with activation of the JNK subgroup but not the ERK subgroup of mitogen-activated protein kinases. *Mol Cell Biol.* 14:6683-6688.

33. Mueller, B. K. 1999. Growth cone guidance: first steps towards a deeper understanding. *Annu Rev Neurosci.* 22:35-388.

34. Newsome, T. P., S. Schmidt, G. Dietzl, K. Keleman, B. Asling, A. Debant, and B. J. Dickson 2000. Trio combines with dock to regulate Pak activity during photoreceptor axon pathfinding in Drosophila. *Cell* 101:283-94.

35. Nobes, C. D., and A. Hall 1995. Rho, rac, and cdc42 GTPases regulate the assembly of multimolecular focal complexes associated with actin stress fibers, lamellipodia, and filopodia. *Cell* 81:53-62.

36. Qu, J., M. S. Cammarano, Q. Shi, K. C. Ha, P. de Lanerolle, and A. Minden 2001. Activated PAK4 Regulates Cell Adhesion and Anchorage-Independent Growth. *Mol Cell Biol.* 21:3523-3533.

37. Ridley, A. J., and A. Hall 1992. The small GTP-binding protein rho regulates the assembly of focal adhesions and actin stress fibers in response to growth factors. *Cell* 70:389-399.

38. Ridley, A. J., H. F. Paterson, C. L. Johnston, D. Diekmann, and A. Hall 1992. The small GTP-binding protein rac regulates growth factor-induced membrane ruffling. *Cell* 70:401-410.

39. Sander, E. E., J. P. ten Klooster, S. van Delft, R. A. van der Kammen, and J. G. Collard 1999. Rac downregulates Rho activity: Reciprocal balance between both GTPases determines cellular morphology and migratory behavior. *J Cell Biol.* 147:1009-1022.

40. Sarner, S., R. Kozma, S. Ahmed, and L. Lim 2000. Phosphatidylinositol 3-Kinase, Cdc42, and Rac1 Act Downstream of Ras in Integrin-Dependent Neurite Outgrowth in N1E-115 Neuroblastoma Cells Mol Cell Biol. 20:158-172.

41. Sastry, P. S., and K. S. Rao 2000. Apoptosis and the nervous system. *J Neurochem.* 74:1-20.

42. Self, A. J., and A. Hall 1995. Purification of recombinant Rho/Rac/G25K from *Escherichia coli*. *Meth Enzymol.* 256:3-10.

43. Sells, M. A., and J. Chernoff 1997. Emerging from the Pak: the p21-activated protein kinase family. *Trends Cell Biol.* 7:162-167.

44. Sells, M. A., U. G. Knaus, S. Bagrodia, D. M. Ambrose, G. M. Bokoch, and J. Chernoff 1997. Human p21-activated kinase (Pak1) regulates actin organization in mammalian cells. *Curr Biol.* 7:202-210.

45. Serafini, T., S. A. Colamarino, E. D. Leonardo, H. Wang, R. Beddington, W. C. Skarnes, and M. Tessier-Lavigne 1996. Netrin-1 is required for commissural axon guidance in the developing vertebrate nervous system. *Cell* 87:1001-1014.

46. Stanyon, C. A., and O. Bernard 1999. LIM-kinase1. *Int J Biochem Cell Biol.* 31:389-394.

47. Steven, R., T. J. Kubiseski, H. Zheng, S. Kulkami, J. Mancillas, A. R. Morales, C. W. V. Hogue, T. Pawson, and J. Culotti 1998. UNC-73 activates the Rac GTPase and is required for cell growth cone migrations in *C. elegans*. *Cell* 92:785-795.

48. Taylor, S. S., D. R. Knighton, J. Zheng, L. F. Ten Eyck, and J. M. Sowadski 1992. Structural framework for the protein kinase family. *Annu Rev Cell Biol.* 8:429-462.

49. Tigyi, G., D. J. Fischer, A. Sebok, F. Marshall, D. L. Dyer, and R. Miledi 1996. Lysophosphatidic acid-induced neurite retraction in PC12 cells: neurite-protective effects of cyclic AMP signaling. *J Neurochem.* 66:549-558.

50. Tigyi, G., D. J. Fischer, A. Sebok, C. Yang, D. L. Dyer, and R. Miledi 1996. Lysophosphatidic acid-induced neurite retraction in PC12 cells: control by phosphoinositide-$Ca^{2+}$ signaling and Rho. *J Neurochem.* 66:537-548.

51. van Leeuwen, F. N., H. E. Kain, R. A. van der Kammen, F. Michiels, O. W. Kranenburg, and J. G. Collard 1997. The guanine nucleotide exchange factor Tiam1 affects neuronal morphology; opposing roles for the small GTPases Rac and Rho. *J Cell Biol.* 139:797-807.

52. Zhang, S. J. Han, M. A. Sells, J. Chernoff, U. G. Knaus, R. J. Ulevitch, and G. M. Bokoch 1995. Rho family GTPases regulate p38 mitogen-activated protein kinase through the downstream mediator Pak1. *J Biol Chem.* 270:23934-23936.

53. Zipkin, I. D., R. M. Kindt, and C. J. Kenyon 1997. Role of a New Rho Family Member in Cell Migration and Axon Guidance in *C. elegans*. *Cell* 90:883-894.

What is claimed is:

1. An isolated nucleic acid that encodes a p21-activated kinase 5 GTPase-binding domain contained within consecutive amino acid residues 10-30 of SEQ ID NO:4, but does not encode consecutive amino acid residues 452-702 of SEQ ID NO:4.

2. An isolated nucleic acid that encodes a p21-activated kinase 5 kinase domain contained within consecutive amino acid residues 452-702 of SEQ ID NO:4, but does not encode consecutive amino acid residues 10-30 of SEQ ID NO:4.

3. An isolated nucleic acid which comprises nucleotides encoding a human p21-activated kinase 5 kinase domain contained within consecutive amino acid residues 452-702 of SEQ ID NO:4 operatively linked to nucleotides encoding an exogenous or endogenous regulatory element, wherein the isolated nucleic acid does not comprise nucleotides encoding a p21-activated kinase 5 GTPase-binding domain contained within consecutive amino acid residues 10-30 of SEQ ID NO:4.

4. The isolated nucleic acid of claim 3, wherein the isolated nucleic acid is DNA.

5. The isolated nucleic acid of claim 3, wherein the isolated nucleic acid is RNA.

6. A vector comprising a nucleic acid which comprises nucleotides encoding a human p21-activated kinase 5 kinase domain contained within consecutive amino acid residues 452-702 of SEQ ID NO:4 operatively linked to nucleotides encoding an exogenous or endogenous regulatory element, wherein the nucleic acid does not comprise nucleotides encoding a p21-activated kinase 5 GTPase-binding domain contained within consecutive amino acid residues 10-30 of SEQ ID NO:4.

7. The vector of claim 6, wherein the vector is selected from the group consisting of a plasmid, a cosmid, a bacteriophage and a eukaryotic virus.

8. The vector of claim 7, wherein the vector is a eukaryotic virus.

9. An isolated host cell which comprises a nucleic acid comprising nucleotides encoding a human p21-activated kinase 5 kinase domain contained within consecutive amino acid residues 452-702 of SEQ ID NO:4 operatively linked to nucleotides encoding an exogenous or endogenous regulatory element, wherein the nucleic acid does not comprise nucleotides encoding a p21-activated kinase 5 GTPase-binding domain contained within consecutive amino acid residues 10-30 of SEQ ID NO:4.

10. The isolated host cell of claim 9, wherein the isolated host cell is selected from the group consisting of a bacterial cell, a fungal cell and an animal cell.

11. The isolated host cell of claim 1 wherein the isolated host cell is an animal cell.

12. A composition comprising the isolated nucleic acid of claim 1 and a pharmaceutically acceptable carrier.

13. A composition comprising the isolated nucleic acid of claim 2 and a pharmaceutically acceptable carrier.

14. A composition comprising the isolated nucleic acid of claim 3 and a pharmaceutically acceptable carrier.

15. The vector of claim 8, wherein the eukaryotic virus is an adenovirus or a retrovirus.

16. The isolated hose cell of claim 11, wherein the animal cell is selected from the group consisting of a neuronal cell, an epithelial cell, a muscle cell, a blood cell, an immune cell, a stem cell, an osteocyte and an endothelial cell.

* * * * *

SEQUENCE LISTING

<160> NUMBER OF SEQ ID NOS: 8

<210> SEQ ID NO 1
<211> LENGTH: 2160
<212> TYPE: DNA
<213> ORGANISM: mouse
<220> FEATURE:
<221> NAME/KEY: misc_feature
<223> OTHER INFORMATION: mouse PAK5

<400> SEQUENCE: 1

```
atgtttggga agaaaaagaa aaagatcgaa atatctggcc catccaactt tgaacacagg      60
gttcatactg gatttgatcc acaagagcag aagtttactg gccttcccca gcagtggcac     120
agcctgttag cagacacagc caacaggccc aagcccatgg tggacccatc atgcatcaca     180
cccatacagc tggctcccat gaagacaatc gtcagaggaa ataaatcctg caaggaaacc     240
tctatcaatg gtctgctaga ggattttgac aacatctccg tgactcgctc caactctcta     300
aggaaagaaa gcccacccac cccagatcag ggagcagcta gccgcattca aggccactcg     360
gaagagaacg gcttcatcac tttctcacaa tattccagtg aatccgatac gactgcggac     420
tacacaactg aaaagtacag agacaggagt ctctatggag atgacctgga tctgtactat     480
aaaagcagcc atgcagccaa gcaaaatggg catgccatga gatgaaaca tggagacgct     540
tactaccctg agatgaagtc tttgaaaacc gacctggccg gattccctgt cgactatcac     600
acccacttgg actctctgag aaaatcaagt gaatatggtg accttaggtg ggattatcag     660
agagcctcta gtagctcccc tctggactac tcattccagc tcacgccttc tagaactgca     720
gggaccagca ggtgctccaa ggagagtctg gcatacagtg aaagtgattg ggacccagc     780
ctggatgact atgacaggag gccaaaatca tcatacctgc atcagacgag ccctcagcca     840
gccatgcgcc agagatccaa gtccggctca gggcttcagg aacccatgat gccatttgga     900
gcaagtgcat taaaaactca tcctcaagga cactcgtaca actcctacac ctaccctcga     960
ttgtccgagc ccacaatgtg cattccaaag gtggattacg atcgagcaca gatggtcttc    1020
agtcctccac tgtcagggtc cgacacttac cccagaggcc ccaccaaact acctcaaagt    1080
caaagcaaag caggctactc ttcaggcagc caccagtacc cttctgggta ccacaaagca    1140
tctctatacc accatccatc cctgcaaacc agttctcagt acatctccac cgcttcttac    1200
ttaagctctc tcagtatctc ctcgagcacc taccctccac ctagctgggg ctcctcctca    1260
gaccagcagc cctcaagggt atcccatgaa caattccgag ctgccctgca actggtggtc    1320
agcccaggag accccaggga atatttggat aactttatta aaatcggaga agggtcgaca    1380
ggcatcgtgt gcattgcaac agagaaacac acaggcaagc aagtggcagt gaagaaaatg    1440
gacctccgaa agcagcagag acgggaactc cttttttaatg aggtcgtgat aatgcgtgat    1500
taccaccatg acaacgtagt tgacatgtac aacagctacc ttgttggaga tgagctctgg    1560
gtggtcatgg agtttctaga aggtggtgcc ttgacagaca ttgtcactca taccagaatg    1620
aatgaagagc agatagctac tgtctgcctg tcagttctga agctctgtc ctaccttcat    1680
aaccaaggag tgattcacag ggacataaag agtgactcca ttcttctgac aagcgatggc    1740
cggataaagt tatctgactt tggtttctgt gctcaagttt ccaaagaggt gccaaagagg    1800
aagtcactgg tgggtacccc atactggatg cacctgaggt gatttccag gctaccttat    1860
gggacagagg tggacatctg gtccctcggg ataatggtga tagagatgat tgatgggag    1920
```

-continued

```
cccccctatt tcaatgagcc tcctctgcag gccatgagga ggatccggga cagtttacct      1980
ccaagagtga aggacctaca caaggtttct tccatgctcc gaggattcct agatcttatg      2040
ttggtgaggg agccctctcg aagagccaca gctcaagaac tccttggaca tccattctta      2100
aaattggcag gtccaccatc ttgcattgtt cctctcatga gacaatacag acatcactga      2160
```

<210> SEQ ID NO 2
<211> LENGTH: 719
<212> TYPE: PRT
<213> ORGANISM: mouse
<220> FEATURE:
<221> NAME/KEY: MISC_FEATURE
<223> OTHER INFORMATION: mouse PAK5

<400> SEQUENCE: 2

```
Met Phe Gly Lys Lys Lys Lys Ile Glu Ile Ser Gly Pro Ser Asn
 1               5                  10                  15

Phe Glu His Arg Val His Thr Gly Phe Asp Pro Gln Glu Gln Lys Phe
                20                  25                  30

Thr Gly Leu Pro Gln Gln Trp His Ser Leu Leu Ala Asp Thr Ala Asn
            35                  40                  45

Arg Pro Lys Pro Met Val Asp Pro Ser Cys Ile Thr Pro Ile Gln Leu
        50                  55                  60

Ala Pro Met Lys Thr Ile Val Arg Gly Asn Lys Ser Cys Lys Glu Thr
65                  70                  75                  80

Ser Ile Asn Gly Leu Leu Glu Asp Phe Asp Asn Ile Ser Val Thr Arg
                85                  90                  95

Ser Asn Ser Leu Arg Lys Glu Ser Pro Pro Thr Pro Asp Gln Gly Ala
                100                 105                 110

Ala Ser Arg Ile Gln Gly His Ser Glu Glu Asn Gly Phe Ile Thr Phe
            115                 120                 125

Ser Gln Tyr Ser Ser Glu Ser Asp Thr Thr Ala Asp Tyr Thr Thr Glu
        130                 135                 140

Lys Tyr Arg Asp Arg Ser Leu Tyr Gly Asp Asp Leu Asp Leu Tyr Tyr
145                 150                 155                 160

Lys Ser Ser His Ala Ala Lys Gln Asn Gly His Ala Met Lys Met Lys
                165                 170                 175

His Gly Asp Ala Tyr Tyr Pro Glu Met Lys Ser Leu Lys Thr Asp Leu
            180                 185                 190

Ala Gly Phe Pro Val Asp Tyr His Thr His Leu Asp Ser Leu Arg Lys
        195                 200                 205

Ser Ser Glu Tyr Gly Asp Leu Arg Trp Asp Tyr Gln Arg Ala Ser Ser
    210                 215                 220

Ser Ser Pro Leu Asp Tyr Ser Phe Gln Leu Thr Pro Ser Arg Thr Ala
225                 230                 235                 240

Gly Thr Ser Arg Cys Ser Lys Glu Ser Leu Ala Tyr Ser Glu Ser Asp
                245                 250                 255

Trp Gly Pro Ser Leu Asp Asp Tyr Asp Arg Arg Pro Lys Ser Ser Tyr
            260                 265                 270

Leu His Gln Thr Ser Pro Gln Pro Ala Met Arg Gln Arg Ser Lys Ser
        275                 280                 285

Gly Ser Gly Leu Gln Glu Pro Met Met Pro Phe Gly Ala Ser Ala Phe
    290                 295                 300

Lys Thr His Pro Gln Gly His Ser Tyr Asn Ser Tyr Thr Tyr Pro Arg
305                 310                 315                 320
```

```
Leu Ser Glu Pro Thr Met Cys Ile Pro Lys Val Asp Tyr Asp Arg Ala
            325                 330                 335

Gln Met Val Phe Ser Pro Pro Leu Ser Gly Ser Asp Thr Tyr Pro Arg
            340                 345                 350

Gly Pro Thr Lys Leu Pro Gln Ser Gln Ser Lys Ala Gly Tyr Ser Ser
            355                 360                 365

Gly Ser His Gln Tyr Pro Ser Gly Tyr His Lys Ala Ser Leu Tyr His
            370                 375                 380

His Pro Ser Leu Gln Thr Ser Ser Gln Tyr Ile Ser Thr Ala Ser Tyr
385                 390                 395                 400

Leu Ser Ser Leu Ser Ile Ser Ser Ser Thr Tyr Pro Pro Ser Ser Trp
                405                 410                 415

Gly Ser Ser Asp Gln Gln Pro Ser Arg Val Ser His Glu Gln Phe
            420                 425                 430

Arg Ala Ala Leu Gln Leu Val Val Ser Pro Gly Asp Pro Arg Glu Tyr
            435                 440                 445

Leu Asp Asn Phe Ile Lys Ile Gly Glu Gly Ser Thr Gly Ile Val Cys
            450                 455                 460

Ile Ala Thr Glu Lys His Thr Gly Lys Gln Val Ala Val Lys Lys Met
465                 470                 475                 480

Asp Leu Arg Lys Gln Gln Arg Arg Glu Leu Leu Phe Asn Glu Val Val
                485                 490                 495

Ile Met Arg Asp Tyr His His Asp Asn Val Val Asp Met Tyr Asn Ser
                500                 505                 510

Tyr Leu Val Gly Asp Glu Leu Trp Val Val Met Glu Phe Leu Glu Gly
            515                 520                 525

Gly Ala Leu Thr Asp Ile Val Thr His Thr Arg Met Asn Glu Glu Gln
            530                 535                 540

Ile Ala Thr Val Cys Leu Ser Val Leu Lys Ala Leu Ser Tyr Leu His
545                 550                 555                 560

Asn Gln Gly Val Ile His Arg Asp Ile Lys Ser Asp Ser Ile Leu Leu
                565                 570                 575

Thr Ser Asp Gly Arg Ile Lys Leu Ser Asp Phe Gly Phe Cys Ala Gln
            580                 585                 590

Val Ser Lys Glu Val Pro Lys Arg Lys Ser Leu Val Gly Thr Pro Tyr
            595                 600                 605

Trp Met Ala Pro Glu Val Ile Ser Arg Leu Pro Tyr Gly Thr Glu Val
            610                 615                 620

Asp Ile Trp Ser Leu Gly Ile Met Val Ile Glu Met Ile Asp Gly Glu
625                 630                 635                 640

Pro Pro Tyr Phe Asn Glu Pro Leu Gln Ala Met Arg Arg Ile Arg
                645                 650                 655

Asp Ser Leu Pro Pro Arg Val Lys Asp Leu His Lys Val Ser Ser Met
            660                 665                 670

Leu Arg Gly Phe Leu Asp Leu Met Leu Val Arg Glu Pro Ser Gln Arg
            675                 680                 685

Ala Thr Ala Gln Glu Leu Leu Gly His Pro Phe Leu Lys Leu Ala Gly
            690                 695                 700

Pro Pro Ser Cys Ile Val Pro Leu Met Arg Gln Tyr Arg His His
705                 710                 715

<210> SEQ ID NO 3
<211> LENGTH: 2160
<212> TYPE: DNA
```

<213> ORGANISM: Homo sapiens
<220> FEATURE:
<221> NAME/KEY: misc_feature
<223> OTHER INFORMATION: Human PAK5

<400> SEQUENCE: 3

| | | | | | |
|---|---|---|---|---|---|
| atgtttggga | agaaaaagaa | aaagattgaa | atatctggcc | cgtccaactt | tgaacacagg | 60 |
| gttcatactg | ggtttgatcc | acaagagcag | aagtttaccg | gccttcccca | gcagtggcac | 120 |
| agcctgttag | cagatacggc | aacaggcca | aagcctatgg | tggacccttc | atgcatcaca | 180 |
| cccatccagc | tggctcctat | gaagacaatc | gttagaggaa | acaaaccctg | caaggaaacc | 240 |
| tccatcaacg | gcctgctaga | ggattttgac | aacatctcgg | tgactcgctc | caactcccta | 300 |
| aggaaagaaa | gcccacccac | cccagatcag | ggagcctcca | gccacggtcc | aggccacgcg | 360 |
| gaagaaaatg | gcttcatcac | cttctcccag | tattccagcg | aatccgatac | tactgctgac | 420 |
| tacacgaccg | aaaagtacag | ggagaagagt | ctctatggag | atgatctgga | tccgtattat | 480 |
| agaggcagcc | acgcagccaa | gcaaaatggg | cacgtaatga | aaatgaagca | cggggaggcc | 540 |
| tactattctg | aggtgaagcc | tttgaaatcc | gattttgcca | gattttctgc | cgattatcac | 600 |
| tcacatttgg | actcactgag | caaaccaagt | gaatacagtg | acctcaagtg | ggagtatcag | 660 |
| agagcctcga | gtagctcccc | tctggattat | tcattccaat | tcacaccttc | tagaactgca | 720 |
| gggaccagcg | ggtgctccaa | ggagagcctg | gcgtacagtg | aaagtgaatg | ggacccagc | 780 |
| ctggatgact | atgacaggag | gccaaagtct | tcgtacctga | atcagacaag | ccctcagccc | 840 |
| accatgcggc | agaggtccag | gtcaggctcg | ggactccagg | aaccgatgat | gccatttgga | 900 |
| gcaagtgcat | ttaaaaccca | tccccaagga | cactcctaca | actcctacac | ctaccctcgc | 960 |
| ttgtccgagc | ccacaatgtg | cattccaaag | gtggattacg | atcgagcaca | gatggtcctc | 1020 |
| agccctccac | tgtcagggtc | tgacacctac | ccaggggcc | ctgccaaact | acctcaaagt | 1080 |
| caaagcaaat | cgggctattc | ctcaagcagt | caccagtacc | gtctgggta | ccacaaagcc | 1140 |
| accttgtacc | atcaccctc | cctgcagagc | agttcgcagt | acatctccac | ggcttcctac | 1200 |
| ctgagctccc | tcagcctctc | atccagcacc | taccgcgc | ccagctgggg | ctcctcctcc | 1260 |
| gaccagcagc | cctccagggt | gtcccatgaa | cagtttcggg | cggccctgca | gctggtggtc | 1320 |
| agcccaggag | accccaggga | atacttggcc | aactttatca | aaatcgggga | aggctcaacc | 1380 |
| ggcatcgtat | gcatcgccac | cgagaaacac | acagggaaac | aagttgcagt | gaagaaaatg | 1440 |
| gacctccgga | agcaacagag | acgagaactg | cttttcaatg | aggtcgtgat | catgcgggat | 1500 |
| taccaccatg | acaatgtggt | tgacatgtac | agcagctacc | ttgtcggcga | tgagctctgg | 1560 |
| gtggtcatgg | agtttctaga | aggtggtgcc | ttgacagaca | ttgtgactca | caccagaatg | 1620 |
| aatgaagaac | agatagctac | tgtctgcctg | tcagttctga | gagctctctc | ctaccttcat | 1680 |
| aaccaaggag | tgattcacag | ggacataaaa | agtgactcca | tcctcctgac | aagcgatggc | 1740 |
| cggataaagt | tgtctgattt | tggtttctgt | gctcaagttt | ccaaagaggt | gccgaagagg | 1800 |
| aaatcattgg | ttggcactcc | ctactggatg | gcccctgagg | tgatttctag | gctaccttat | 1860 |
| gggacagagg | tggacatctg | gtccctcggg | atcatggtga | tagaaatgat | tgatggcgag | 1920 |
| cccccctact | tcaatgagcc | tccctccag | gcgatgcgga | ggatccggga | cagtttacct | 1980 |
| ccaagagtga | aggacctaca | caaggtttct | tcagtgctcc | ggggattcct | agacttgatg | 2040 |
| ttggtgaggg | agccctctca | gagagcaaca | gcccaggaac | tcctcggaca | tccattctta | 2100 |
| aaactagcag | gtccaccgtc | ttgcatcgtc | cccctcatga | gacaatacag | gcatcactga | 2160 |

```
<210> SEQ ID NO 4
<211> LENGTH: 719
<212> TYPE: PRT
<213> ORGANISM: Homo sapiens
<220> FEATURE:
<221> NAME/KEY: MISC_FEATURE
<223> OTHER INFORMATION: Human PAK5

<400> SEQUENCE: 4

Met Phe Gly Lys Lys Lys Lys Ile Glu Ile Ser Gly Pro Ser Asn
1               5                   10                  15

Phe Glu His Arg Val His Thr Gly Phe Asp Pro Gln Glu Gln Lys Phe
                20                  25                  30

Thr Gly Leu Pro Gln Gln Trp His Ser Leu Leu Ala Asp Thr Ala Asn
            35                  40                  45

Arg Pro Lys Pro Met Val Asp Pro Ser Cys Ile Thr Pro Ile Gln Leu
        50                  55                  60

Ala Pro Met Lys Thr Ile Val Arg Gly Asn Lys Pro Cys Lys Glu Thr
65                  70                  75                  80

Ser Ile Asn Gly Leu Leu Glu Asp Phe Asp Asn Ile Ser Val Thr Arg
                85                  90                  95

Ser Asn Ser Leu Arg Lys Glu Ser Pro Pro Thr Pro Asp Gln Gly Ala
                100                 105                 110

Ser Ser His Gly Pro Gly His Ala Glu Glu Asn Gly Phe Ile Thr Phe
            115                 120                 125

Ser Gln Tyr Ser Ser Glu Ser Asp Thr Thr Ala Asp Tyr Thr Thr Glu
        130                 135                 140

Lys Tyr Arg Glu Lys Ser Leu Tyr Gly Asp Asp Leu Asp Pro Tyr Tyr
145                 150                 155                 160

Arg Gly Ser His Ala Ala Lys Gln Asn Gly His Val Met Lys Met Lys
                165                 170                 175

His Gly Glu Ala Tyr Tyr Ser Glu Val Lys Pro Leu Lys Ser Asp Phe
            180                 185                 190

Ala Arg Phe Ser Ala Asp Tyr His Ser His Leu Asp Ser Leu Ser Lys
        195                 200                 205

Pro Ser Glu Tyr Ser Asp Leu Lys Trp Glu Tyr Gln Arg Ala Ser Ser
    210                 215                 220

Ser Ser Pro Leu Asp Tyr Ser Phe Gln Phe Thr Pro Ser Arg Thr Ala
225                 230                 235                 240

Gly Thr Ser Gly Cys Ser Lys Gly Ser Leu Ala Tyr Ser Glu Ser Glu
                245                 250                 255

Trp Gly Pro Ser Leu Asp Asp Tyr Asp Arg Arg Pro Lys Ser Ser Tyr
            260                 265                 270

Leu Asn Gln Thr Ser Pro Gln Pro Thr Met Arg Gln Arg Ser Arg Ser
        275                 280                 285

Gly Ser Gly Leu Gln Glu Pro Met Met Pro Phe Gly Ala Ser Ala Phe
    290                 295                 300

Lys Thr His Pro Gln Gly His Ser Tyr Asn Ser Tyr Thr Tyr Pro Arg
305                 310                 315                 320

Leu Ser Glu Pro Thr Met Cys Ile Pro Lys Val Asp Tyr Asp Arg Ala
                325                 330                 335

Gln Met Val Leu Ser Pro Pro Leu Ser Gly Ser Asp Thr Tyr Pro Arg
            340                 345                 350

Gly Pro Ala Lys Leu Pro Gln Ser Gln Ser Lys Ser Gly Tyr Ser Ser
        355                 360                 365
```

```
Ser Ser His Gln Tyr Pro Ser Gly Tyr His Lys Ala Thr Leu Tyr His
    370                 375                 380

His Pro Ser Leu Gln Ser Ser Gln Tyr Ile Ser Thr Ala Ser Tyr
385                 390                 395                 400

Leu Ser Ser Leu Ser Leu Ser Ser Thr Tyr Pro Pro Ser Trp
                405                 410                 415

Gly Ser Ser Asp Gln Gln Pro Ser Arg Val Ser His Glu Gln Phe
                420                 425                 430

Arg Ala Ala Leu Gln Leu Val Val Ser Pro Gly Asp Pro Arg Glu Tyr
                435                 440                 445

Leu Ala Asn Phe Ile Lys Ile Gly Glu Gly Ser Thr Gly Ile Val Cys
450                 455                 460

Ile Ala Thr Glu Lys His Thr Gly Lys Gln Val Ala Val Lys Lys Met
465                 470                 475                 480

Asp Leu Arg Lys Gln Gln Arg Arg Glu Leu Leu Phe Asn Glu Val Val
                485                 490                 495

Ile Met Arg Asp Tyr His His Asp Asn Val Val Asp Met Tyr Ser Ser
                500                 505                 510

Tyr Leu Val Gly Asp Glu Leu Trp Val Val Met Glu Phe Leu Glu Gly
                515                 520                 525

Gly Ala Leu Thr Asp Ile Val Thr His Thr Arg Met Asn Glu Glu Gln
                530                 535                 540

Ile Ala Thr Val Cys Leu Ser Val Leu Arg Ala Leu Ser Tyr Leu His
545                 550                 555                 560

Asn Gln Gly Val Ile His Arg Asp Ile Lys Ser Asp Ser Ile Leu Leu
                565                 570                 575

Thr Ser Asp Gly Arg Ile Lys Leu Ser Asp Phe Gly Phe Cys Ala Gln
                580                 585                 590

Val Ser Lys Glu Val Pro Lys Arg Lys Ser Leu Val Gly Thr Pro Tyr
                595                 600                 605

Trp Met Ala Pro Glu Val Ile Ser Arg Leu Pro Tyr Gly Thr Glu Val
                610                 615                 620

Asp Ile Trp Ser Leu Gly Ile Met Val Ile Glu Met Ile Asp Gly Glu
625                 630                 635                 640

Pro Pro Tyr Phe Asn Glu Pro Leu Gln Ala Met Arg Arg Ile Arg
                645                 650                 655

Asp Ser Leu Pro Pro Arg Val Lys Asp Leu His Lys Val Ser Ser Val
                660                 665                 670

Leu Arg Gly Phe Leu Asp Leu Met Leu Val Arg Glu Pro Ser Gln Arg
                675                 680                 685

Ala Thr Ala Gln Glu Leu Leu Gly His Pro Phe Leu Lys Leu Ala Gly
                690                 695                 700

Pro Pro Ser Cys Ile Val Pro Leu Met Arg Gln Tyr Arg His
705                 710                 715

<210> SEQ ID NO 5
<211> LENGTH: 7
<212> TYPE: PRT
<213> ORGANISM: Homo sapiens

<400> SEQUENCE: 5

Ala Pro Ser Asn Phe Glu His
1               5
```

<210> SEQ ID NO 6
<211> LENGTH: 20
<212> TYPE: DNA
<213> ORGANISM: Homo sapiens

<400> SEQUENCE: 6
agtagggagt gccaaccaat                                           20

<210> SEQ ID NO 7
<211> LENGTH: 591
<212> TYPE: PRT
<213> ORGANISM: Homo sapiens

<400> SEQUENCE: 7

Met Phe Gly Lys Arg Lys Lys Arg Val Glu Ile Ser Ala Pro Ser Asn
1               5                   10                  15

Phe Glu His Arg Val His Thr Gly Phe Asp Gln His Glu Gln Lys Phe
            20                  25                  30

Thr Gly Leu Pro Arg Gln Trp Gln Ser Leu Ile Glu Ser Ala Arg
        35                  40                  45

Arg Pro Lys Pro Leu Val Asp Pro Ala Cys Ile Thr Ser Ile Gln Pro
    50                  55                  60

Gly Ala Pro Lys Thr Ile Val Arg Gly Ser Lys Gly Ala Lys Asp Gly
65                  70                  75                  80

Ala Leu Thr Leu Leu Leu Asp Glu Phe Glu Asn Met Ser Val Thr Arg
                85                  90                  95

Ser Asn Ser Leu Arg Arg Asp Ser Pro Pro Pro Ala Arg Ala Arg
            100                 105                 110

Gln Glu Asn Gly Met Pro Glu Glu Pro Ala Thr Thr Ala Arg Gly Gly
        115                 120                 125

Pro Gly Lys Ala Gly Ser Arg Gly Arg Phe Ala Gly His Ser Glu Ala
    130                 135                 140

Gly Gly Gly Ser Gly Asp Arg Arg Ala Gly Pro Glu Lys Arg Pro
145                 150                 155                 160

Lys Ser Ser Arg Glu Gly Ser Gly Gly Pro Gln Glu Ser Ser Arg Asp
                165                 170                 175

Lys Arg Pro Leu Ser Gly Pro Asp Val Gly Thr Pro Gln Pro Ala Gly
            180                 185                 190

Leu Ala Ser Gly Ala Lys Leu Ala Ala Gly Arg Pro Phe Asn Thr Tyr
        195                 200                 205

Pro Arg Ala Asp Thr Asp His Pro Ser Arg Gly Ala Gln Gly Glu Pro
    210                 215                 220

His Asp Val Ala Pro Asn Gly Pro Ser Ala Gly Gly Leu Ala Ile Pro
225                 230                 235                 240

Gln Ser Ser Ser Ser Ser Arg Pro Pro Thr Arg Ala Arg Gly Ala
                245                 250                 255

Pro Ser Pro Gly Val Leu Gly Pro His Ala Ser Glu Pro Gln Leu Ala
            260                 265                 270

Pro Pro Ala Cys Thr Pro Ala Ala Pro Ala Val Pro Gly Pro Pro Gly
        275                 280                 285

Pro Arg Ser Pro Gln Arg Glu Pro Gln Arg Val Ser His Glu Gln Phe
    290                 295                 300

Arg Ala Ala Leu Gln Leu Val Val Asp Pro Gly Asp Pro Arg Ser Tyr
305                 310                 315                 320

Leu Asp Asn Phe Ile Lys Ile Gly Glu Gly Ser Thr Gly Ile Val Cys
                325                 330                 335

-continued

Ile Ala Thr Val Arg Ser Ser Gly Lys Leu Val Ala Val Lys Lys Met
                340                 345                 350

Asp Leu Arg Lys Gln Gln Arg Arg Glu Leu Leu Phe Asn Glu Val Val
            355                 360                 365

Ile Met Arg Asp Tyr Gln His Glu Asn Val Val Glu Met Tyr Asn Ser
        370                 375                 380

Tyr Leu Val Gly Asp Glu Leu Trp Val Val Met Glu Phe Leu Glu Gly
385                 390                 395                 400

Gly Ala Leu Thr Asp Ile Val Thr His Thr Arg Met Asn Glu Glu Gln
                405                 410                 415

Ile Ala Ala Val Cys Leu Ala Val Leu Gln Ala Leu Ser Val Leu His
            420                 425                 430

Ala Gln Gly Val Ile His Arg Asp Ile Lys Ser Asp Ser Ile Leu Leu
        435                 440                 445

Thr His Asp Gly Arg Val Lys Leu Ser Asp Phe Gly Phe Cys Ala Gln
    450                 455                 460

Val Ser Lys Glu Val Pro Arg Arg Lys Ser Leu Val Gly Thr Pro Tyr
465                 470                 475                 480

Trp Met Ala Pro Glu Leu Ile Ser Arg Leu Pro Tyr Gly Pro Glu Val
                485                 490                 495

Asp Ile Trp Ser Leu Gly Ile Met Val Ile Glu Met Val Asp Gly Glu
            500                 505                 510

Pro Pro Tyr Phe Asn Glu Pro Leu Lys Ala Met Lys Met Ile Arg
        515                 520                 525

Asp Asn Leu Pro Pro Arg Leu Lys Asn Leu His Lys Val Ser Pro Ser
    530                 535                 540

Leu Lys Gly Phe Leu Asp Arg Leu Leu Val Arg Asp Pro Ala Gln Arg
545                 550                 555                 560

Ala Thr Ala Ala Glu Leu Leu Lys His Pro Phe Leu Ala Lys Ala Gly
                565                 570                 575

Pro Pro Ala Ser Ile Val Pro Leu Met Arg Gln Asn Arg Thr Arg
            580                 585                 590

<210> SEQ ID NO 8
<211> LENGTH: 681
<212> TYPE: PRT
<213> ORGANISM: Homo sapiens

<400> SEQUENCE: 8

Met Phe Arg Lys Lys Lys Lys Arg Pro Glu Ile Ser Ala Pro Gln
1               5                   10                  15

Asn Phe Gln His Arg Val His Thr Ser Phe Asp Pro Lys Glu Gly Lys
                20                  25                  30

Phe Val Gly Leu Pro Pro Gln Trp Gln Asn Ile Leu Asp Thr Leu Arg
            35                  40                  45

Arg Pro Lys Pro Val Val Asp Pro Ser Arg Ile Thr Arg Val Gln Leu
        50                  55                  60

Gln Pro Met Lys Thr Val Val Arg Gly Ser Ala Met Pro Val Asp Gly
65                  70                  75                  80

Tyr Ile Ser Gly Leu Leu Asn Asp Ile Gln Lys Leu Ser Val Ile Ser
                85                  90                  95

Ser Asn Thr Leu Arg Gly Arg Ser Pro Thr Ser Arg Arg Ala Gln
            100                 105                 110

Ser Leu Gly Leu Leu Gly Asp Glu His Trp Ala Thr Asp Pro Asp Met

-continued

```
                115                 120                 125
Tyr Leu Gln Ser Pro Gln Ser Glu Arg Thr Asp Pro His Gly Leu Tyr
            130                 135                 140
Leu Ser Cys Asn Gly Gly Thr Pro Ala Gly His Lys Gln Met Pro Trp
145                 150                 155                 160
Pro Glu Pro Gln Ser Pro Arg Val Leu Pro Asn Gly Leu Ala Ala Lys
                165                 170                 175
Ala Gln Ser Leu Gly Pro Ala Glu Phe Gln Gly Ala Ser Gln Arg Cys
            180                 185                 190
Leu Gln Leu Gly Ala Cys Leu Gln Ser Ser Pro Gly Ala Ser Pro
            195                 200                 205
Pro Thr Gly Thr Asn Arg His Gly Met Lys Ala Ala Lys His Gly Ser
    210                 215                 220
Glu Glu Ala Arg Pro Gln Ser Cys Leu Val Gly Ser Ala Thr Gly Arg
225                 230                 235                 240
Pro Gly Gly Glu Gly Ser Pro Ser Pro Lys Thr Arg Glu Ser Ser Leu
                245                 250                 255
Lys Arg Arg Leu Phe Arg Ser Met Phe Leu Ser Thr Ala Ala Thr Ala
            260                 265                 270
Pro Pro Ser Ser Ser Lys Pro Gly Pro Pro Gln Ser Lys Pro Asn
            275                 280                 285
Ser Ser Phe Arg Pro Pro Gln Lys Asp Asn Pro Pro Ser Leu Val Ala
    290                 295                 300
Lys Ala Gln Ser Leu Pro Ser Asp Gln Pro Val Gly Thr Phe Ser Pro
305                 310                 315                 320
Leu Thr Thr Ser Asp Thr Ser Ser Pro Gln Lys Ser Leu Arg Thr Ala
                325                 330                 335
Pro Ala Thr Gly Gln Leu Pro Gly Arg Ser Ser Pro Ala Gly Ser Pro
            340                 345                 350
Arg Thr Trp His Ala Gln Ile Ser Thr Ser Asn Leu Tyr Leu Pro Gln
            355                 360                 365
Asp Pro Thr Val Ala Lys Gly Ala Leu Ala Gly Glu Asp Thr Gly Val
    370                 375                 380
Val Thr His Glu Gln Phe Lys Ala Ala Leu Arg Met Val Val Asp Gln
385                 390                 395                 400
Gly Asp Pro Arg Leu Leu Leu Asp Ser Tyr Val Lys Ile Gly Glu Gly
                405                 410                 415
Ser Thr Gly Ile Val Cys Leu Ala Arg Glu Lys His Ser Gly Arg Gln
            420                 425                 430
Val Ala Val Lys Met Met Asp Leu Arg Lys Gln Gln Arg Arg Glu Leu
            435                 440                 445
Leu Phe Asn Glu Val Val Ile Met Arg Asp Tyr Gln His Phe Asn Val
    450                 455                 460
Val Glu Met Tyr Lys Ser Tyr Leu Val Gly Glu Glu Leu Trp Val Leu
465                 470                 475                 480
Met Glu Phe Leu Gln Gly Gly Ala Leu Thr Asp Ile Val Ser Gln Val
                485                 490                 495
Arg Leu Asn Glu Glu Gln Ile Ala Thr Val Cys Glu Ala Val Leu Gln
            500                 505                 510
Ala Leu Ala Tyr Leu His Ala Gln Gly Val Ile His Arg Asp Ile Lys
            515                 520                 525
Ser Asp Ser Ile Leu Leu Thr Leu Asp Gly Arg Val Lys Leu Ser Asp
    530                 535                 540
```

```
Phe Gly Phe Cys Ala Gln Ile Ser Lys Asp Val Pro Lys Arg Lys Ser
545                 550                 555                 560

Leu Val Gly Thr Pro Tyr Trp Met Ala Pro Glu Val Ile Ser Arg Ser
                565             570                 575

Leu Tyr Ala Thr Glu Val Asp Ile Trp Ser Leu Gly Ile Met Val Ile
            580             585                 590

Glu Met Val Asp Gly Glu Pro Pro Tyr Phe Ser Asp Ser Pro Val Gln
        595             600             605

Ala Met Lys Arg Leu Arg Asp Ser Pro Pro Lys Leu Lys Asn Ser
        610             615             620

His Lys Val Ser Pro Val Leu Arg Asp Phe Leu Glu Arg Met Leu Val
625                 630             635                 640

Arg Asp Pro Gln Glu Arg Ala Thr Ala Gln Glu Leu Leu Asp His Pro
                645             650                 655

Phe Leu Leu Gln Thr Gly Leu Pro Glu Cys Leu Val Pro Leu Ile Gln
            660             665             670

Leu Tyr Arg Lys Gln Thr Ser Thr Cys
        675             680
```